US007682615B2

(12) United States Patent
Kristiansen

(10) Patent No.: US 7,682,615 B2
(45) Date of Patent: *Mar. 23, 2010

(54) IMMUNE MODULATING COMPOUNDS FROM FUNGI

(75) Inventor: Bjørn Kristiansen, Frederikstad (NO)

(73) Assignee: BeKa Holding AS (NO)

( * ) Notice: Subject to any disclaimer, the term of this patent is extended or adjusted under 35 U.S.C. 154(b) by 0 days.

This patent is subject to a terminal disclaimer.

(21) Appl. No.: 11/657,722

(22) Filed: Jan. 25, 2007

(65) Prior Publication Data

US 2008/0031892 A1 Feb. 7, 2008

Related U.S. Application Data

(63) Continuation-in-part of application No. 10/892,393, filed on Jul. 16, 2004, now Pat. No. 7,514,085.

(60) Provisional application No. 60/690,496, filed on Jun. 15, 2005, provisional application No. 60/690,477, filed on Jun. 15, 2005, provisional application No. 60/690,482, filed on Jun. 15, 2005.

(51) Int. Cl.
*A61K 36/06* (2006.01)

(52) U.S. Cl. .................................. 424/195.15

(58) Field of Classification Search ....................... None
See application file for complete search history.

(56) References Cited

U.S. PATENT DOCUMENTS

| 3,943,247 A | 3/1976 | Komatsu |
| 3,987,166 A | 10/1976 | Komatsu et al. |
| 4,163,780 A | 8/1979 | Ishida et al. |
| 4,174,388 A | 11/1979 | McAleer et al. |
| 4,207,312 A | 6/1980 | Fujii et al. |
| 4,247,541 A | 1/1981 | Ishida et al. |
| 4,281,061 A * | 7/1981 | Zuk et al. ................... 435/7.9 |
| 4,454,289 A | 6/1984 | Nakajima et al. |
| 4,461,760 A | 7/1984 | Sugano |
| 4,617,379 A | 10/1986 | Dobkin et al. |
| 4,769,363 A | 9/1988 | Misaki et al. |
| 4,851,395 A | 7/1989 | Ueno et al. |
| 4,962,094 A | 10/1990 | Jamas et al. |
| 5,032,401 A | 7/1991 | Jamas et al. |
| 5,223,491 A | 6/1993 | Donzis |
| 5,281,577 A * | 1/1994 | Koga et al. ................... 514/2 |
| 5,283,239 A | 2/1994 | Koga |
| 5,322,841 A | 6/1994 | Jamas et al. |
| 5,397,773 A | 3/1995 | Donzis |
| 5,488,040 A | 1/1996 | Jamas et al. |
| 5,504,079 A | 4/1996 | Jamas et al. |
| 5,519,009 A | 5/1996 | Donzis |
| 5,532,223 A | 7/1996 | Jamas et al. |
| 5,576,015 A | 11/1996 | Donzis |
| 5,607,677 A | 3/1997 | Jamas et al. |
| 5,622,939 A | 4/1997 | Jamas et al. |
| 5,622,940 A | 4/1997 | Ostroff |
| 5,633,369 A | 5/1997 | Jamas et al. |
| 5,641,761 A | 6/1997 | Takahashi |
| 5,663,324 A | 9/1997 | James et al. |
| 5,702,719 A | 12/1997 | Donzis |
| 5,705,184 A | 1/1998 | Donzis |
| 5,741,495 A | 4/1998 | Jamas et al. |
| 5,744,187 A | 4/1998 | Gaynor |
| 5,756,318 A | 5/1998 | Kosuna |
| 5,783,569 A | 7/1998 | Jamas et al. |
| 5,811,542 A | 9/1998 | Jamas et al. |
| 5,817,643 A | 10/1998 | Jamas et al. |
| 5,849,720 A | 12/1998 | Jamas et al. |
| 5,998,173 A * | 12/1999 | Haynes et al. ................. 435/84 |
| 6,020,324 A | 2/2000 | Jamas et al. |
| 6,046,323 A | 4/2000 | Park |
| 6,084,092 A | 7/2000 | Wakshull et al. |
| 6,090,615 A | 7/2000 | Nagaoka |
| 6,090,938 A | 7/2000 | Wakshull et al. |
| 6,110,892 A | 8/2000 | Barbier et al. |
| 6,117,850 A | 9/2000 | Patchen et al. |
| 6,120,772 A | 9/2000 | Ito |
| 6,143,731 A | 11/2000 | Jamas et al. |
| 6,294,321 B1 | 9/2001 | Wakshull et al. |
| 6,297,363 B1 * | 10/2001 | Kubo et al. ................. 536/17.4 |
| 6,369,216 B1 | 4/2002 | Patchen et al. |
| 6,413,715 B2 | 7/2002 | Wakshull et al. |

(Continued)

FOREIGN PATENT DOCUMENTS

CN          1082551          2/1994

(Continued)

OTHER PUBLICATIONS

Aoki, et al., "Antibodies to HTLV I and III in sera from two Japanese patients, one with possible pre-AIDS", *The Lancet*, Oct. 20, 1984.
Aoki, "Lentinan", *Immune Modulation Agents and Their Mechanisms*, Editors: Fenichel and Chirigos, Marcel Dekker, Inc. 1984, pp. 63-77.
Chiara, et al., "Antitumor Polysaccharide derived Chemically from Natural Glucan (Pachyman)", *Nature*, vol. 225, Mar. 7, 1970.
Chiara, "The antitumor polysaccharide Lentinan: An Overview", *Manipulation of Host Defence Mechanisms*, Editors: Aoki, et al., *Excerpta Medica* 1981, pp. 1-16.
Hamuro, J. et al., "Carboxymethlpachymaran, a New Water Soluble Polysaccharide with Marked Antitumor Activity", *Nature* vol. 233, Oct. 15, 1971.

(Continued)

*Primary Examiner*—Christopher R. Tate
*Assistant Examiner*—Deborah A. Davis
(74) *Attorney, Agent, or Firm*—Davis Wright Tremaine LLP

(57) ABSTRACT

The present invention relates to compositions comprising polypeptides and polysaccharides. The compositions are in general immune modulating. The invention also discloses methods of producing these compositions using filamentous fungi cultivated in liquid medium. The compositions are useful for example in the treatment of immune compromised conditions.

10 Claims, No Drawings

U.S. PATENT DOCUMENTS

| | | |
|---|---|---|
| 6,440,448 B1 | 8/2002 | Intelisano |
| 6,630,310 B1 | 10/2003 | Wakshull et al. |
| 6,692,739 B1 | 2/2004 | Patti et al. |
| 6,702,999 B2* | 3/2004 | Lawlor ..................... 424/48 |
| 7,022,685 B2 | 4/2006 | Patchen et al. |
| 2001/0051717 A1 | 12/2001 | Wakshull et al. |
| 2002/0164317 A1 | 11/2002 | Gorsek |
| 2002/0164773 A1 | 11/2002 | Wasser |
| 2003/0208796 A1 | 11/2003 | Song et al. |
| 2005/0002962 A1 | 1/2005 | Pasco et al. |
| 2005/0069989 A1 | 3/2005 | Kim et al. |
| 2005/0130273 A1 | 6/2005 | Versali |
| 2005/0158258 A1 | 7/2005 | Fisher |
| 2005/0163800 A1 | 7/2005 | Kristiansen |
| 2005/0238654 A1 | 10/2005 | Takeda |
| 2005/0245480 A1 | 11/2005 | Ostroff et al. |
| 2006/0013825 A1 | 1/2006 | Kristiansen |
| 2006/0159698 A1 | 7/2006 | Murata et al. |
| 2007/0041994 A1 | 2/2007 | McDowell |
| 2007/0104728 A1 | 5/2007 | Olalde Rangel |
| 2007/0172934 A1 | 7/2007 | Muller et al. |
| 2007/0178118 A1 | 8/2007 | Goino |
| 2008/0063650 A1 | 3/2008 | Yan |
| 2008/0103112 A1 | 5/2008 | Magee et al. |
| 2008/0106114 A1 | 5/2008 | Wheatley |
| 2008/0167268 A1 | 7/2008 | Yan |

FOREIGN PATENT DOCUMENTS

| | | |
|---|---|---|
| CN | 1269423 | 11/2000 |
| CN | 1297994 | 6/2001 |
| CN | 1314417 | 9/2001 |
| CN | 1477130 | 2/2004 |
| CN | 1490016 | 4/2004 |
| CN | 1528335 | 9/2004 |
| CN | 1765935 | 3/2006 |
| EP | 0 292 601 | 11/1988 |
| EP | 0 298 706 | 1/1989 |
| EP | 0 298 706 | 11/1989 |
| EP | 0 370 673 | 5/1990 |
| EP | 0382551 | 8/1990 |
| EP | 1155623 | 11/2001 |
| GB | 1331513 A | 9/1973 |
| JP | 5653101 | 5/1981 |
| JP | 01132315 | 5/1989 |
| JP | 06172217 | 6/1994 |
| JP | 7173070 | 7/1995 |
| JP | 63296662 | 12/1998 |
| JP | 11080206 | 3/1999 |
| JP | 2001-078714 | 3/2001 |
| JP | 2002060344 | 2/2002 |
| JP | 2004300438 | 3/2004 |
| KR | 470734 | 2/2005 |
| KR | 2003097062 | 2/2005 |
| SU | 1244179 A | 7/1986 |
| WO | WO 89/12106 | 12/1989 |
| WO | WO 8912106 | 12/1989 |
| WO | WO 91/06307 | 5/1991 |
| WO | WO 96/15659 | 5/1996 |
| WO | WO 00/32212 | 6/2000 |
| WO | WO 00/32213 | 6/2000 |
| WO | WO 00/54795 | 9/2000 |
| WO | WO 00/65029 | 11/2000 |
| WO | WO 0151070 | 7/2001 |
| WO | WO 01/64057 | 9/2001 |
| WO | WO 01/82935 | 11/2001 |
| WO | WO 02/07708 | 1/2002 |
| WO | WO 02/087603 | 11/2002 |
| WO | WO 02/098440 | 12/2002 |
| WO | WO 03/020944 | 3/2003 |
| WO | WO 03/043440 | 5/2003 |
| WO | WO 03/049117 A2 | 6/2003 |
| WO | WO 03/080077 | 10/2003 |
| WO | WO 2004/075907 | 9/2004 |
| WO | WO 2004/100965 | 11/2004 |
| WO | WO 2005/044182 | 5/2005 |
| WO | WO 2006/007848 | 1/2006 |
| WO | WO 2006133707 | 12/2006 |

OTHER PUBLICATIONS

Sassaki, et al., "Further study of the structure of lentinan, an antitumor polysacchride from Lentinus edodes", *Carbohydrate Research*, 47 (1976) 99-104.

Suzuki, et al., "Structural characterization of the Immunoactive and Antiviral Water-solubilized Lignin in an Extract of the Culture Medium of *Lentinus edodes* Mycelia (LEM)".

Suzuki, et al., "Induction of endogenous lymphokine-activated killer activity by combined administration of lentinan and interleukin 2", *Int J. Immunopharmac*. vol. 12, No. 6, pp. 613-623, 1990.

Tokimoto, K., "Lysis of the mycelium of Lentinus edodes caused by mycolytic enzymes of *Trichoderma harzianum* when two fungi were in an antagonistic state", *Trans. Mycol. Soc*. Japan 23:13-20, 1982.

S. Aouadi et al., "Structural analysis and rheological behaviour of an extracellular polysaccharide from *Drechslera spicifera*", *Carbohydrate Polymers*, vol. 17 pp. 177-183, 1992.

Giovanni Giovannozzi Sermanni et al., "The Production of Exo-Enzymes by *Lentinus edodes* and *Pleurotus ostreatus* and their use for Upgrading Corn Straw", *Bioresource Technology*, vol. 48, pp. 173-178, 1994.

Byung-Keun Yang et al., "Hypoglycemic Effect of a *Lentinus edodes* Exo-polymer Produced from a Submerged Mycelial Culture", *Biosci. Biotechnol. Biochem*. vol. 66:5, pp. 937-942, 2002.

Nora Hatvani, "Antibacterial effect of the culture fluid of *Lentinus edodes* mycelium grown in submerged liquid culture", *International Journal of Antimicrobial Agents*, vol. 17, pp. 71-74, 2001.

Zhou Weidong et. al., "Biological activity of hydrosoluble exopolysaccharide (HEP) from *Lentinus edodes* CL-2 by submerged fermentation", *Junwu Xitong*, vol. 16, No. 3, p. 202-207, 1997.

Zheng Xueyu et al., "Immune function of the extracellular and intracellular polysaccharides of *Lentinus edodes*", *Zhongcaoyao*, vol. 16, No. 11, p. 494-497, 1985 [The Study of the Effect of LNT and HEP of *Lentinus edodes* on the Immune of Normal Mice].

Gou et al. Effects of mushroom and herb polysaccharides, as alternatives for an antibiotic, on growth performance of broilers. British Poultry Science vol. 45, No. 5, p. 684-694, Oct. 2004.

Lobanok et al. Composition and biological activity of submerged mycelium of the xylotrophic basidiomycete *lentinus edodes*. Applied Biochemistry and microbiology, vol. 39, No. 1, 2003, p. 60-64 (translated from Priki Biokhi Mikkrobiol Jan.-Feb. 2003, 39(1):69-73).

Van Nevel et al.,"The influence of *Lentinus edodes* (Shiitake muhroom) preparations on bacteriological and morphological aspects of the small intestine in piglets", Archives of animal nutrition—archive fur tierernahrung 57(6):399-412, Dec. 2003 (abstract).

Kawazoe T, et al. ,"Influence of an excessive supply of vitamin D-1 fortified shiitake mushroom on laying hens", Journal of the Japanese Society for food and science technology—Nippon Shokuhin Kagaku Kaishi 44(4) :300-305, 1997 (Abstract).

Gou FC, et al., "Effects of mushroom and herb polysaccharides, as alternatives for an antibiotic, on the cecal microbial ecosystm in broiler chickens", Poultry Science 83(2): 175-182 Feb. 2004 (abstract).

Gou et al. , "Immunoactive, medicinal properties of mushroom and herb polysaccharides and their potential use in chicken diets", Worlds poultry science journal 59(4) : 427-440 Dec. 2003 (abstract).

Nikl L et al., "Influence of 7 immunostimulants on the immne-response of Coho Salmon to Aeromonas-salmonicida", Diseases of Aquatic organisms 12(1): 7-12 Dec. 5, 1991 (Abstract).

Xueyu Z, et al. The study of the effect of LNT and HEP of *Lentinus edodes* on the immune of normal mice. (Guangxi institute of traditional Chinese medicine and material medica).

Song CH, et al. Anti-complementary activity of endo-polymers produced from submerged mycelial culture of higher fungi with particular reference to *Lentinus edodes*. Biotechnology Letters, vol. 20, No. 8, Aug. 1998, pp. 741-744.

Synopsis: Chapter 5: Extraction, development and chemistry of anticancer compounds from medicinal mushrooms, pp. 80-105.

Borchers A., et al. Mushrooms, Tumors, and Immunity: An update., Experimental Biology and Medicine, 229:393-406 (2004).

Fujimiya et al., Selective Tumoricidal effect of soluble proteoglucan extracted from the basidiomycete, *Agaricus blazei* Murill, mediated via natural killer cell activation and apoptosis, Cancer Immunol Immunother (1998) 46: 147-159.

Kobayashi et al., "Suppressing effects of daily oral supplementation of beta-glucan extracted from *Agaricus blazei* Murill on spontaneous and peritoneal disseminated metastasis in mouse model", J Cancer Res Clin Oncol. May 10, 2005 pp. 1-20.

Mizuno et al., "Anti-tumor polysaccharide from the mycelium of liquid-cultured *Agaricus blazei* mill", Biochem Mol Biol Int. Apr. 1999;47(4):707-14.

Ohno et al., Antitumor beta glucan from the cultured fruit body of *Agaricus blazei*. Biol Pharm Bull. Jul. 2001;24(7):820-8.

Fujimiya et al., Tumor-specific cytocidal and immunopotentiating effects of relatively low molecular weight products derived from the basidiomycete, *Agaricus blazei* Murill. Anticancer Res. Jan.-Feb. 1999;19(1A):113-8.

Takaku et al., Isolation of an antitumor compound from *Agaricus blazei* Murill and its mechanism of action. J Nutr. May 2001;131(5):1409-13.

Ito et al., "Antitumout effects of a new polysaccharide-protein complex (ATOM) prepared from *Agaricus blazei* (Iwade strain 101) "Himematsutake" and its mechanisms in tumor-bearing mice", Anticancer research 17:277-284 (1997).

Kawagishi et al., Formolysis of a potent antitumor (1-6)-beta-D-glucan-protein complex from *Agaricus blazei* fruiting bodies and antitumor activity of the resulting products. Carbohydr polymers 12:393-403, 1990.

Abstract: Osaki, Y., et al. "Antimutagenic and bactericidal substances in the fruit body of a Basidiomycete *Agaricus blazei*, Jun-17", Yakugaku Zasshi, vol. 114(5), pp. 342-350, 1994.

Liu et al., "Fractionation of extracellular polysaccharide from *Agaricus blazei* murill and its antitumor activity", Shipin Yu Fajiao Gongye (2001), 27(11), 27-29.

Gonzaga et al., "Isolation and characterization of polysaccharides from *Agaricus blazei* Murill", Carbohydrate polymers 2005, vol. 60, Iss 1, p. 43-49.

Kimura et al., "Isolation of an anti-angiogenic substance from *Agaricus blazei* Murill: Its antitumor and antimetastatic actions", Cancer Science, Sep. 2004, vol. 95, Iss 9, p. 758-764.

Griffin et al., "Free lipids and carbohydrates of *Agaricus bisporus* mycelium", Biochem J. Sep. 1970; 119(3):11P-12P.

Shu CH; Wen BJ; Lin KJ "Monitoring the polysaccharide quality of *Agaricus blazei* in submerged culture by examining molecular weight distribution and TNF-alpha release capability of macrophage cell line RAW 264.7" Biotechnology Letters 2003, vol. 25, Iss 24, pp. 2061-2064.

Mizuno T. The extraction and development of antitumor-active polysaccharides from medicinal mushrooms in Japan [Review]. International Journal of Medicinal Mushrooms 1999;1:9-29.

Fan et al., "Production of polysaccharide by culinary-medicinal mushroom *Agaricus brasiliensis* S Wasser et al. LPB 03 (Agaricomycetideae) in submerged fermentation and its antitumor effect", International Journal of Medicinal Mushrooms (2003), 5(1), 17-23.

Abstract: Liu et al., "Study on antitumor activity of *Agaricus blazei*", Shipin Gongye Kenji (2001), 22(4), 10-11.

Kimura, Y: In Vivo 2005, vol. 19, Iss 1, p. 37-60; "New Anticancer agents: In Vitro and In Vivo Evaluation of the antitumor and Antimetastatic Actions of Various Compounds Isolated from Medicinal Plants".

Kuo et al., Journal of Laboratory and clinical medicine, Sep. 2002, vol. 140, Iss 3, p. 176-187; "Cell Cycle progression and cytokine gene expression of human peripheral blood mononuclear cells modulated by *Agaricus blazei*".

Ooi et al., Current Medicinal Chemistry 2000, vol. 7, Iss 7, p. 715-729; "Immunomodulation and Anti-Cancer Activity of Polysaccharide-Protein Complexes".

Sorimachi et al., Cell structure and function 2001, vol. 26, Iss 2, p. 103-108, "Secretion of TNF-alpha, IL-8 and Nitric Oxide by Macrophages Activated with *Agaricus blazei* Murrill fractions in vitro".

Zhang, L., et al. "Correlation between antitumor activity, molecular weight, and conformation of lentinan" Carbohydrate Research, 340, (2005), 1515-1521.

Kim, S.W., et al. "Mycelial growth and exo-biopolymer production by submerged culture of various edible mushrooms under different media". Letters in applied Microbiology, 2002, 34,56-61, XP001051185.

Jong, S.C., and Birmingham, J.M. "Medicinal and Therapeutic Value of the Shiitake Mushroom". Advances in applied microbiology, 1993, vol. 39, 1993, pp. 153-184, XP008056557.

U.S. Appl. No. 11/657,722, filed Jan. 25, 2007, Kristiansen.

U.S. Appl. No. 11/661,551, filed Mar. 1, 2007, Kristiansen.

U.S. Appl. No. 11/917,521, Kristiansen.

Wasser: "Medical mushrooms as a source of antitumor and immunomodulating polysaccharides" Applied Microbial Biotechnology, vol. 60, 2002, pp. 258-274, XP002402437 * See p. 258 (left col.), p. 261 (Table 1/*Agaricus*), p. 263 (Table 2/*Agaricus*), pp. 268-269 (*A. blazei*), and pp. 270-271 (Conclusions), the whole document *.

Shu et al: "Effects of culture pH on the production of bioactive polysaccharides by *Agaricus blazei* in batch cultures" Journal of Chemical Technology and Biotechnology, vol. 79, 2004, pp. 998-1002, XP001235865 * See p. 998 (Introduction) and p. 1001 (left column); early on-line publication *.

Fan et al: "Effect of nutritional and environmental conditions on the production of exo-polysaccharide of *Agaricus brasiliensis* by sub-merged fermentation and its antitumor activity" LWT, vol. 40, Oct. 20, 2005, pp. 30-35, XP005582762 * See pp. 30-31 (Abstract and Introduction); early on-line publication*.

Brauer et al. Effects of Management on the Yield and High-Molecular-weight Polysaccharide Content of Shiitake (*Lentinus edodes*) Mushrooms. J Agric Food Chem 2002, pp. 5333-5337, vol. 50, p. 5333, col. 2, paragraph 2, p. 5334, col. 1, paragraph 3-col. 2, paragraph 1.

Elisashvili et al. Extracellular Polysaccharide Production by Culinary- Medicinal Shiitake Mushroom *Lentinus edodes* (Berk.) Singer and *Pleurotus* (Fr.) P. Karst. Species Depending on Carbon and Nitrogen Source. International Journal of Medicinal Mushrooms, 2004, pp. 165-172, vol. 6.

Zorn et al. Enzymatic hydrolysis of carotenoid esters of marigold lowers (*Tagetes erecta* L.) and red paprika (*Capsicum annuum* L.) by commercial lipases and *Pleurotus sapidus* extracellular lipase. Enzyme and Microbial Technology, 2003, pp. 623-628, vol. 32, Elsevier, ISSN: 0141-0229 p. 623, col. 1, p. 624, col. 2, paragraph 3.

Lee et al. Submerged culture conditions for the production of mycelial biomass and exopolysaccharides by the edible Basidiomycete *Grifola frondosa*. Enzyme and Microbial Technology 2004, pp. 369-376, vol. 35, Elsevier. ISSN: 0141-0229 p. 369, col. 1-2, p. 370, col. 2, paragraph 3-p. 371, col. 1, paragraph 1.

Kondhkar et al. Sugar profile of extracellular polysaccharides from different *Tremella* species. International Journal of Food Microbiology, 2002, pp. 121-129, vol. 79, Elsevier.

Hsieh et al. Production of polysaccharides of *Ganoderma lucidum* (CCRC36021) by reusing thin stillage. Process Biochemistry 2005 vol. 40, No. 2, Feb. 2005, pp. 909-916, XP004647027 ISSN: 1359-5113 p. 909, col. 2, paragraph 1, p. 910, col. 1, paragraph 4-col. 2, paragraph 2, p. 915, col. 1, paragraph 3.

Lee, et al. "Structural Analysis of the Antitumor Active Exo-polysaccharide Produced by Submerged Cultivation of *Ganoderma lucidum* Mycelium", The Korean Journal of Mycology, vol. 27, No. 1, pp. 76-81, Feb. 1999. English abstract.

Li, et al., "Isolation, Purification and Bioactivities of Exopoly Saccharides from Fermented Broth of *Ganoderma lucidum*", Acta Microbiologica Sinica, vol. 40, No. 2, pp. 217-220, Apr. 2000. English abstract.

Yang, et al., "Hepatoprotective Effect of exo-polysaccharide Produced from Submerged Mycelial Culture of Ganoderma lucidum WK-003 by using Industrial Grade Medium", The Korean journal of Mycology, vol. 27, No. 1, pp. 82-86, Feb. 1999. English abstract.

Yang, et al., "The influence of environmental conditions on polysaccharide formation by Ganoderma lucidum in submerged cultures", Process Biochemistry, vol. 33, No. 5, pp. 547-553, 1998.

Kim D-H et al: "Production of a hypoglycemic, extracellular polysaccharide from the submerged culture of the mushroom, Phellinus linteus" Biotechnology Letters, KEW, Surrey, GB, vol. 23, Apr. 2001, pp. 513-517, XP008017803, ISSN:0141-5492 p. 513, col. 2, paragraph 2 figure 1; table 3.

Tan YH and Moore D "Convenient and effective methods for in vitro cultivation of mycelium and fruiting bodies of Lentinus edodes" Mycol. Res., 1992, 96(12): 1077-1084, abstract, materials & methods, and results & discussion.

MediMush Science Documents. K. Tuberculosis. Downloaded from Medimush website Jun. 2005 (www.medimush.dk), pp. 1-2, Oct. 2004.

MediMush Science Documents. H. Lentinan taken orally. Downloaded from Medimush website Jun. 2005 (www.medimush.dk), pp. 1-5, Oct. 2004.

Chang R. Functional properties of edible mushrooms. Nutrition Reviews, vol. 54, No. 11. Nov. 1996: s91-s93.

Harvey, L et al. Production of Lentinan by submerged cultivation of Lentinus edodes (Berk.) Sing. Int. Jour. Of Medicinal Mushrooms, vol. 3, p. 161 (2001).

Wasser SP and Weis AL, Medicinal properties of substances occurring in higher basidiomyces mushrooms: current perspectives (Review). International Journal of Medicinal Mushrooms, 1999, vol. 1: 31-62, entire document.

The term "Extracellular"—Merriam-Webster Online Dictionary, at www.m-w.com. p. 1.

MediMush Science Documents. C. Immune modifiers from the shiitake mushroom. Downloaded from Medimush website Jun. 2005, pp. 1-9, Oct. 2004.

MediMush Science Documents. L. HIV/AIDS. Downloaded from Medimush website Jun. 2005 (www.medimush.dk), pp. 1-3, Oct. 2004.

Kim, S.W., et al., "Mycelial growth and exo-biopolymer production by submerged culture of various edible mushrooms under different media", Letters in applied Microbiology, 2002, 34, 56-61, XP001051185.

Jong, S.C., and Birmingham, J.M., "Medicinal and Therapeutic Value of the Shiitake Mushroom", Advances in applied microbiology, 1993, vol. 39, pp. 153-184, XP008056557.

Yamashita, et al., "Intestinal absorption and urinary excretion of antibumor peptidomannan KS-2 after oral administration in rats", Immunopharmacology, Feb. 1983; 5(3):209-20.

Maeda, et al., "Partial purification of lentinan-induced factors that cause vascular dilatation and hemorrhage or increase of acute-phase proteins in mice", Supplied by the British Library—"The world's knowledge", pp. 167-176.

Allison, et al., "Unique increase of serum proteins and action of antitumour polysaccharides", Nature, vol. 252, Nov. 15, 1974, pp. 250-252.

Fujii, et al., "Isolation and characterization of a new antitumour polysaccharide, KS-2, extracted from culture mycelia of Lentinus edodes", J. Antibiot (Tokyo), Nov. 1978, 31(11):1079-90.

Maeda, et al., "Denaturation and renaturation of beta-1, 6; 1,3-glucan, lentinan, associated with expression of T-cell-mediated responses", Cancer research 48, 671-675, Feb. 1, 1988.

Suzuki, et al., "Antiviral and interferon-inducing activities of a new peptidomannan, KS-2, extracted from culture mycelia of Lentinus edodes", j. Antibiot (Tokyo), Dec. 1979; 32(12):1336-45.

Chihara, et al., "Fractionation and purification of the polysaccharides with marked antitumor activity, especially lentinan, from lentinus edodes (Berk.) Sing. (an edible mushroom)", Cancer research, 30, 2776-2781, Nov. 1970.

O'Neil, et al., eds. The Merck Index ($14^{th}$ ed. 2006), p. 941 (entry 5439 "Lentinan").

Eureka Bio-Chemicals Specifications for "Lentinan for Injection", website www.biochem.com.au/specs.htm, pp. 1 and 7-9 of 16 pp., accessed Jan. 3, 2008.

Wang, Tze-Hua, et al., "Lentinus Products and Patents in China". Medimush internal document, compiled from information retrieved from internet Aug.-Sep. 2006.

Chihara et al., "Fractionation and purification of the polysaccharides with marked antitumor activity, especially lentinan, from Lentinus edodes (Berk.) Sing. (an edible mushroom)", Cancer research, 30, 2775-2781, 1970.

Jin Y et al., "Antitumor activities of heteropolysaccharides of Poria cocos mycelia from different strains and culture media", Carbohydrate Research 2003, 338: 1517-1521.

Peng Y et al, "Structure and antitumor activity of extracellular polysaccharides from mycelium", Carbohydrate Polymers 2003, 54, 297-303.

Sasaki et al.: "Further study of the structure of lentinan, an anti-tumor polysaccharide from Lentinus edodes" Carbohydrate Research, 47 (1976) 99-104.

Togami M et al., "Studies on basidiomycetes I antitumor polysaccharide from bagasse medium on which mycelia of Lentinus edodes (Berk.) Sing. had been grown", Chem Pharm Bull 1982, 30: 1134-1140.

Wang H et al, "Lectins from mushrooms", Mycol Res 1998, 102:897-906.

Zhang M et al., "Molecular weight and anti-tumor activity of the water-soluble polysaccharides isolated by hot water and ultrasonic treatment from the sclerotia and mycelia of pleurotus tuber-regium", Carbohydrate Polymers, available online Mar. 12, 2004, 56:123-128.

* cited by examiner

IMMUNE MODULATING COMPOUNDS FROM FUNGI

This application is a continuation-in-part of U.S. patent application Ser. No. 10/892,393, filed Jul. 16, 2004, hereby incorporated by reference in its entirety. Related U.S. provisional application Ser. No. 60/690,482, filed Jun. 15, 2005, U.S. provisional application Ser. No. 60/690,496 filed Jun. 15, 2005, and U.S. provisional application Ser. No. 60/690,477, filed 15 Jun. 2005, are also hereby incorporated by reference in their entirety. All patent and non-patent references cited in these patent applications, or in the present application, are hereby incorporated by reference in their entirety.

FIELD OF INVENTION

The present invention relates to immune modulating compounds comprising polysaccharides that may be isolated from a liquid culture of fungi.

BACKGROUND OF INVENTION

It is known that health-promoting effects are attributed to glucans from fungi and yeasts. "Shiitake" fungus (*Lentinus edodes*) has been attributed effects which can be exploited for many medicinal purposes such as immunestimulation, anti-virus, anti-tumor, etc. Studies of lentinan have shown that it stimulates the immune system of the host in a variety of ways, such as activation of T helper cells, increased production of Interleukin 1 and Interleukin 2, increased antibody production in various forms of cancer, and decreasing the cholesterol level in the blood. (Herbs for Health, January/February, 1997; K. Jones, "Shiitake: Medicine in a mushroom", p. 40-50, 54; Anticancer Res, Vol. 17(4A), 1997; H. Matsouka, "Lentinan potentiates immunity and prolongs the survival time of some patients", p. 2751-2755; Adv Appl Microbiol, Vol. 39, 1993; S. C. Jong, "Medicinal and therapeutic value of the shiitake mushroom", p. 153-184, Int J Immunopharmacol, Vol. 14, 1992; K. Irinoda, "Stimulation of microbiocidal host defense mechanism against aerosol influenza virus infection by lentinan, p. 971-977, Jpn J Cancer Res, Vol. 76(1), 1985; D. Herlyn, "Monoclonal antibody-dependent murine macrophage-mediated cytotoxicity against human tumors is stimulated by lentinan, p. 37-42).

One active ingredient of *Lentinus edodes* is termed lentinan, a polysaccharide based compound described as a beta-(1,3) glucan backbone with beta-(1,6) side chains.

"Solid-state" reactors are routinely used for culturing fungi such as *Lentinus edodes*. This is a technology which is used for many purposes such as composting, production of biological products such as enzymes, soy sauce, acetic acid, and the like. For the production of lentinan, *Lentinus edodes* can be cultivated on a suitable solid matrix provided by stems of tree or chips of wood to which is often added chemical compounds supporting the growth of mycelium and development of the fruiting bodies, where most of the lentinan is localised. The fruiting bodies are harvested, either by hand or mechanically, and are subsequently dried and ground to a powder which can be used as it is, or used in tablets, or sent for further processing such as extraction of lentinan.

A polysaccharide product prepared from *Lentinus edode* is commercially available as "Lentinan for injection" (Eureka Bio-Chemicals Pty, Australia). This product has some immunestimulating effect (see also the examples herein below).

The patent application WO03/020944 describes a number of methods of purifying extracellular immunestimulating compounds from fungi. In general these methods involve a precipitation step.

However, compositions with very high immunestimulating activity have not been disclosed. It is therefore an object of the present invention to provide novel compositions, preferably extracellular immune stimulating agents from fungi with high level of immune modulating activity.

SUMMARY OF INVENTION

The present invention discloses compositions comprising polysaccharides with significant immune modulating activity. Interestingly, the present invention discloses that the specific monosaccharide content of a polysaccharide composition is important for the immune modulating activity.

Thus it is one object of the present invention to provide a composition comprising one or more polypeptides and a mixture of polysaccharides, wherein the majority of the polysaccharides of the composition, preferably every polysaccharide has a molecular weight of at least 10,000 Da and wherein said mixture of polysaccharides comprises the monosaccharides galactose, mannose, and glucose in the ratio (0-1.5):(0-0.5) to (15-35):(0.5-1.5) to (45-55), preferably in the ratio of about 1:0 to 25:1 to 50, such as in the ration of 1:0 to 25:1 to 50.

In another embodiment is provided a composition comprising one or more polypeptides and a mixture of polysaccharides, wherein:

a) the majority of the polysaccharides of the composition have a molecular weight of at least 30,000 Da and wherein said mixture of polysaccharides comprises the monosaccharides galactose, mannose and glucose in the ratio 1:0 to 25:1 to 50, or b) the majority of the polysaccharides of the composition have a molecular weight of at least 100,000 Da and wherein said mixture of polysaccharides comprises the monosaccharides galactose, mannose and glucose in the ratio 0 to 0.5:0.5 to 10:0.5 to 50, or c) the majority of the polysaccharides of the composition have a molecular weight of at least 1,000 Da and wherein said mixture of polysaccharides comprises the monosaccharides galactose, mannose and glucose in the ratio 1:0 to 25:1 to 50.

It is a second object of the present invention to provide methods of producing such a composition, said method comprising the steps of i) Cultivating a fungus in a liquid growth medium
ii) Purifying said composition from said liquid growth medium It is a third object of the present invention to provide pharmaceutical compositions comprising the above-mentioned composition and pharmaceutically acceptable carrier (s) for use as a medicament.

It is a further object of the present invention to provide methods of treatment of an individual, said method comprising the steps of administering to said individual the compositions according to the invention in an effective amount.

It is an additional object of the present invention to provide use of the compositions according to the invention in the manufacture of a medicament for treatment, optionally prophylactic treatment of an immune compromised condition of an individual in need of such treatment.

Definitions

Polysaccharides: the term "polysaccharide" as used herein covers polysaccharides as well as polysaccharides containing and/or covalently linked to peptides, polypeptides or the like, such as proteopolysaccharides.

Polysaccharides comprising monosaccharides: A polysaccharide is said to comprise monosaccharides, wherein said monosaccharides are covalently linked to form said polysaccharide. Hydrolysing a polysaccharide will yield the monosaccharides that formed said polysaccharide in free form. The monosaccharide content of a polysaccharide can thus be determined by hydrolysing the polysaccharide and measuring the presence of individual monosaccharides. The monosaccharide content of a mixture of polysaccharides is determined by determining the monosaccharide content of the entire mixture.

Ratio: A polysaccharide or a mixture of polysaccharides are said to comprise galactose, mannose, and glucose in a given ratio, when hydrolysation of said polysaccharide or said mixture of polysaccharide yields galactose, mannose and glucose in said given ratio. Galactose, mannose, and glucose in the ratio 1:a to b:c to d, means that for every part galactose, mannose is present in the range of a to b parts and glucose is present in the range of c to d parts, wherein a, b, c and d indicates numerical values. Thus, by way of example a polysaccharide mixture comprising galactose, mannose, and glucose in the ratio 1:5 to 25:1 to 50, means that for every part galactose, the polysaccharide mixture comprises in the range of 5 to 25 parts mannose and in the range if 1 to 50 part glucose.

Molecular weight: Every polysaccharide of a composition is said to have a molecular weight of at least a given value, when said composition has been purified using a filtration step resulting in a molecular weight cut-off of said given value. Similarly, every polysaccharide of a composition is said to have a molecular weight within a given range, when said composition has been subjected to one or more filtration steps resulting in a lower molecular weight cut-off which is the lower value of the range and an upper molecular weight cut-off which is the upper value of the range. Said filtration step may for example be ultrafiltration, microfiltration, ultra-centrifugation or gel filtration. However, a composition wherein every polysaccharide has a molecular weight of at least a given value or every polysaccharide is said to have a molecular weight within a given range may also be prepared by other methods.

Polypeptide: the term "polypeptide" as used herein covers proteins, peptides and polypeptides, wherein said proteins, peptides or polypeptides may or may not have been post-translationally modified. Post-translational modification may for example be phosphorylation, methylation, glucosylation.

DETAILED DESCRIPTION OF THE INVENTION

Composition

The compositions according to the present invention comprise one or more polypeptides and a mixture of polysaccharides. Said polypeptides may optionally be covalently linked to polysaccharides. It is however also comprised within the present invention that said polypeptides are either not associated with said polysaccharides or that said polypeptides are associated with said polysaccharides in a non-covalent manner.

Thus the compositions comprise polysaccharides which may or may not be proteopolysaccharides, or the compositions may comprise a mixture of both.

The compositions according to the present invention are isolated or purified compositions, i.e. they have been subjected to one or more purification steps. In a preferred embodiment they have been purified from liquid growth medium of a fungal mycelium using at least one purification step comprising a size fractionation. Methods of purification are described in more detail below.

In a preferred embodiment, the composition essentially consists of polysaccharides and optionally polypeptides, more preferably the composition essentially consists of polysaccharides and polypeptides. Frequently, the composition is a liquid composition, and it is then preferred that the composition essentially consists of polysaccharides and optionally polypeptides dissolved in an aqueous solution optionally comprising salts and buffer.

The polysaccharides of the compositions of the invention preferably comprises the monosaccharides glucose, mannose and galactose. Examples of polysaccharides and polypeptides that may be comprised within the compositions of the invention include, but are not limited to, $\beta$-(1,3), $\beta$-(1,6) D-glucans, schizophyllan, grifolan, coriolan and *Coriolus versicolor* glycosylated polypeptides such as PSK and PSP, polypeptides associated with alpha-mannan such as KS-2, which may be isolated from *Lentinus edodes*, and reishi, which may be isolated from *Ganoderma lucidum*; glucuron-oxylomannans; mannoglucans; glucomannans; galactoglucan and/or *galactoglucomannans*.

Fungi

In a preferred embodiment of the present invention the compositions disclosed herein have been produced by a fungus. Preferably, the compositions have been purified from the extracellular environment of a fungus. Even more preferably the fungus, preferably a fungal mycelium, has been cultivated in a liquid growth medium and said composition has been purified from said liquid growth medium.

It is thus preferred that the composition of the invention has been produced by a method comprising the steps of
 i) cultivating a fungus, such as a fungal mycelium, in a liquid growth medium, and
 ii) isolating the composition from said liquid growth medium By fungal mycelium is intended any fungal biomass, which can be grown in a submerged culture. The fungal biomass may be in the form of single hyphae, spores, aggregates of mycelium, and partly differentiated mycelium.

The liquid growth medium may be any of the liquid growth media described herein below.

The fungus may be any fungus, preferably a fungus forming a fungal mycelium, more preferably the fungus is a filamentous fungus. Even more preferably, the fungus may be selected from the group consisting of *Agaricus bisporus, Cordiceps sinensis, Flammulina velutipes, Ganoderma lucidum, Grifola frondosa, Lentinus edodes, Pleurotus ostreatus, Schizophyllum commune, Sclerotina sclerotium, Trametes (Coriolus) versicolor, Tremella fuciformis, Agaricus blazei, Agrocybe aegerita, Agrocybe cylindracea, Albatrellus confluens, Armillariella mellea, Auricularia auricula-judae, Auricularia polytricha, Collybia maracula, Cordiceps militari, Dendropolyporus umbellatus, Fomes fomentarius, Fomes pinicola, Ganoderma applanatum, Ganoderma tsugae, Hericium erinaceus, Hypsizygus marmoreus, Inonotus obliquus, Laetiporus sulphurous, Lenzites betulinus, Leucopaxilllus giganteus, Lyophyllum cinerascens, Omphalina epichysium, Oudemansiella mucida, Panellus serotinus, Piptoporus betulinus, Phellinus linteus, Phellinus pini, Pholiota nameko, Pleurotus citrinopileatus, Pleurotus pulmonarius, Sarcedon asparatus, Trametes suavolens, Volvariella volvacea* and *Wolfiporia cocos*.

Yet more preferably, the fungus is selected from the group consisting of *Agaricus bisporus, Cordiceps sinensis, Flammulina velutipes, Ganoderma lucidum, Grifola frondosa, Lentinus edodes, Pleurotus ostreatus, Schizophyllum commune, Sclerotina sclerotium, Trametes (Coriolus) versicolor* and *Tremella fuciformis* In another preferred embodiment, the fungus is Agaricus blazei. In another preferred embodiment, said fungus is *Ganoderma*, such as *Ganoderma lucidum*. In another preferred embodiment, the fungus is an *Agaricus* fungus, such as selected from the group consisting of: *A. blazei, A. blazei Murill, A. bisporus, A. hortensis, A. campestris*.

In a very preferred embodiment of the present invention the fungus belongs to the class of basidiomycetes, such as a fungus of the genus *Lentinus*, such as *Lentinus edodes*.

*Lentinus edodes* deposited under IHEM 18992 with the Belgian Coordinated Collections of Microorganism (BCCM), 14 Rue J. Wytsman, B-1050 Bruxelles, Belgium, represents one preferred strain of *Lentinus edodes*. Further strains of *Lentinus edodes* are available from culture collections such as ATCC (American Type Culture Collection, P.O. Box 1549, Manassas, Va. 20108, USA), CBC (Centraalbureau voor Schimmelcultures, PO Box 85167, 3508 AD Utrecht, THE NETHERLANDS) and DSMZ (Deutsche Sammlung von Mikroorganismen und Zellkulturen GmbH, Mascheroder Weg 1b, 38124 Braunschweig GERMANY).

Additionally relevant *Lentinus* species, besides *Lentinus edodes*, includes *Lentinus* species such as: *Lentinus albovelutinus* G. Stev. (1964)=*Rhodocybe albovelutina* (G. Stev.) E. Horak (1971); *Lentinus anthocephalus* (Lév.) Pegler; *Lentinus badius* Bres.; *Lentinus castoreus* Fr. (1838)=*Lentinellus ursinus* (Fr.) Kühner (1926); *Lentinus chrysopeplus* Berk. & M. A. Curtis (1869)=*Cyptotrama asprata* (Berk.) Redhead & Ginns (1980); *Lentinus cochleatus* Fr.; *Lentinus concinnus* Pat.; *Lentinus delicatus* G. Stev. (1964)=*Marasmius delicatus* (G. Stev.) E. Horak (1971); *Lentinus fasciatus* Berk.; *Lentinus hepatotrichus* Berk. (1859)=*Lentinellus ursinus* (Fr.) Kühner (1926); *Lentinus hyracinus* Kalchbr. (1880)=*Lentinellus ursinus* (Fr.) Kühner (1926); *Lentinus lepideus sensu* Colenso (1891); *Lentinus lepideus* (Fr.) Fr. (1825)=*Lentinus suffrutescens* (Brot.) Fr. (1825); *Lentinus novaezelandiae* Berk. (1855)=*Lentinellus ursinus* (Fr.) Kühner (1926); *Lentinus pulvinulus* Berk. (1859)=*Lentinellus pulvinulus* (Berk.) Pegler (1965); *Lentinus punctaticeps* Berk. & Broome (1883); *Lentinus punctaticeps* cf. *sensu* Petersen, Nicholl & Hughes (1997); *Lentinus pygmaeus* Colenso (1887)=*Lentinus zelandicus* Sacc. & Cub. (1887); *Lentinus sajor-caju* (Fr.) Fr.; *Lentinus squarrulosus* Mont.; *Lentinus strigosus* (Schwein.) Fr. (1825); *Lentinus suffrutescens* (Brot.) Fr. (1825); and *Lentinus tuber-regium* Fr.; *Lentinus zelandicus* Sacc. & Cub. (1887) (Ref: http://nzfungi.landcareresearch.co.nz).

Modulation of the Immune System

The compositions according to the invention are preferably immune modulating, preferably, the compositions are immune stimulating. The stimulation of the immune system can be demonstrated by e.g. increased antibody production, by activation of helper T-cells, or by increased production of interleukins such as Interleukin 1 and Interleukin 2.

Any assay known to the skilled person, which is suitable for testing whether a composition is immune modulating may be employed to test whether a composition of the present invention is immune modulating. Such an assay may be an in vitro or an in vivo assay.

One preferred assay is to test whether the composition is capable of inducing IL-1 production, such as IL1-α and/or IL1-β production. Thus, in a preferred embodiment of the invention, the composition according to the present invention is capable of inducing IL-1 production from at least one kind of IL-1 producing cells in an in-vitro assay. The cells may be any IL-1 producing cells, such as P388 mouse macrophage cells. Preferably, said cell is a IL-1beta producing cell. IL-1 production may be determined using any suitable assay. In general, assays involving the use of specific IL-1 antibodies, such as specific IL1-α and/or IL1-β antibodies, are useful. Such assays may for example be Western blotting, ELISA or similar assays. The assay may be performed as described in example 4.

Because it is difficult to calibrate an IL1 assay, the assay is preferably performed using a specific composition as reference. Thus in one preferred embodiment of the present invention, the composition is capable of inducing production of at least 1.5, preferably at least 2, such as at least 4, for example at least 6, such as at least 8, for example at least 10, such as at least 15, for example at least 20, such as at least 30, for example at least 40 times more IL1-α, than the amount of IL1-α induced using the commercially available Lentinan for injection (Eureka Bio-Chemicals Pty, Little Collins Street. Melbourne 3000, Australia) in a reference experiment performed in parallel. In one preferred embodiment of the present invention, the composition is capable of inducing production of at least 1.5, preferably at least 2, such as at least 4, for example at least 6, such as at least 8, for example at least 10, such as at least 15, for example at least 20 times more IL1-β, than the amount of IL1-β induced using Lentinan for injection from Eureka Biochemicals Pty. in a reference experiment performed in parallel. Preferably, the aforementioned assays are performed as described in example 4. It is most preferred that the composition induced production of both IL1α and IL1β as described above.

In another embodiment of the invention, the composition is capable of enhancing antibody production in a mammal, when administered to said mammal. The mammal may for example be a mouse, rat, rabbit or even a human being. Preferably such an assay is performed by administering the composition to a mammal prior to and simultaneously with administration of an antigen, optionally in the presence of an adjuvant. Preferably, the composition is administered in the range of 1 to 30 days, preferably in the range of 1 to 10 days, more preferably in the range of 1 to 3 days prior to administration of the antigen. Subsequently, antibody production in the mammal may be determined. The composition is preferably capable of inducing production of at least 1.5, more preferably at least 2, even more preferably at least 2.5, such as at least 3, for example at least 4, such as 6 times more antibody compared to the amount of antibody produced without administration of the composition. An example of such an assay is outlined in example 6.

It is preferred that the composition is immune modulating in more than one assay system, such as in a combination of any of the assay systems described herein above.

In one preferred embodiment, the compositions of the present invention act to increase TNF-alpha production, such as may be measured by the assay described in Example 9.

Monosaccharide Content

The composition according to the present invention preferably comprises polysaccharides, wherein the majority of the polysaccharides, preferably at least 60%, more preferably at least 70%, even more preferably at least 80%, yet more preferably at least 90%, even more preferably at least 95%, yet more preferably essentially all polysaccharides, most preferably every polysaccharide has a molecular weight above 10,000 Da, preferably above 30,000 Da, more preferably above 40,000 Da, even more preferably above 50,000 Da, for example at least 100,000 Da, such as at least 300,000 Da, for example at least 1,000,000 Da. In one embodiment of the invention the majority of polysaccharides, preferably every polysaccharide of the composition has a molecular weight within the range of 10,000 to 3,000,000 Da., for example within the range of 30,000 to 3,000,000, such as within the range of 40,000 to 3,000,000, for example within the range of 50,000 to 3,000,000, such as in the range of 50,000 to 100,000, for example in the range of 100,000 to 300,000, such as in the range of 300,000, to 1,000,000, for example in the range of 1,000,000 to 3,000,000.

Preferably, the composition has been purified by a method involving at least one size fractionation step. Thus it is preferred, that the composition has been purified using at least one size fractionation step wherein molecules, such as polysaccharides with a nominal molecular weight above a given cut-off are separated from molecules, such as polysaccharides with a nominal molecular weight below said cut-off. By way of example, if the size fractionation is ultrafiltration or microfiltration a membrane with said cut-off may be used. If the size fractionation is gel filtration a gel with said molecular weight cut off may be chosen or a particular elution fraction may be used. In one embodiment of the invention the larger molecular weight fraction is used, wherein the cut-off preferably is 10,000 Da, more preferably 30,000 Da, even more preferably 40,000 Da, yet more preferably 50,000 Da.

In another embodiment of the invention, the composition has been purified by a method involving one or more size fractionation steps, wherein a resulting fraction comprises polysaccharides with a nominal molecular weight below a given cut-off and above a given cut-off. By way of example, if the size fractionation is ultrafiltration or microfiltration, then first one fractionation step using a membrane with the lower molecular weight cut off may be performed. The larger molecular weight fraction may be collected and subjected to a second ultrafiltration or microfiltration using a membrane with the upper molecular weight cut off. After the second filtration step the lower molecular weight fraction may be collected. If gel filtration is used a particular elution fraction may be used. If ultracentrifugation is used, a membrane with the lower molecular cut-off and a membrane with the upper molecular weight cut-off may be used.

The composition according to the present invention comprises a mixture of polysaccharides, wherein said mixture comprises the monosaccharides galactose, mannose, and glucose in the ratio 1:5 to 25:1 to 50. Thus, the ratio reflects the ratio within the entire mixture of polysaccharides. It is thus feasible that each individual polysaccharide within the mixture comprises a different ratio of the monosaccharides.

The ratio may in general be determined by degrading the entire mixture of polysaccharides into monosaccharides and subsequently determining the concentration of each of said monosaccharides. Polysaccharides may be degraded to their constituent monosaccharides by hydrolysis, for example by hydrolysis in a strong acid, such as HCl. The hydrolysate may be analysed by any conventional method available to the skilled person, for example by HPLC, mass spectrometry or NMR.

In one embodiment of the invention the polysaccharides comprise the mono-saccharides glucose and mannose. In another embodiment of the invention the polysaccharides comprise the monosaccharides glucose and galactose. In a preferred embodiment of the invention, the polysaccharides of the composition comprise the monosaccharides galactose, mannose and glucose.

It is preferred that the mixture of polysaccharides comprises in the range of 5 to 25, preferably in the range of 5 to 20, more preferably in the range of 5 to 17, even more preferably in the range of 6 to 15, yet more preferably in the range of 7 to 14, such as in the range of 10 to 17, for example in the range of 11 to 16, such as in the range of 12 to 15, for example in the range of 13 to 14, such as approximately 13.4±0.4, for example 13.4±0.4 parts mannose for every part galactose.

It is preferred that the mixture of polysaccharides comprises in the range of 1 to 50, preferably in the range of 1 to 40, more preferably in the range of 1 to 30, even more preferably in the range of 1 to 25, yet more preferably in the range of 1 to 20, even more preferably in the range of 2 to 15, yet more preferably in the range of 2 to 14, such as in the range of 8 to 17, for example in the range of 9 to 16, such as in the range of 10 to 15, for example in the range of 11 to 14, such as approximately 12.6±1.3, for example 12.6±1.3 parts glucose for every part galactose.

It is even more preferred that the mixture comprises a ratio of mannose to galactose as indicated herein above and a ratio of glucose to galactose in a ratio as indicated herein above.

In embodiments of the invention, wherein the polysaccharides comprise mannose and glucose it is preferred that they comprise in the range of 0.1 to 30, such as in the range of 0.1 to 0.25, for example in the range of 0.25 to 0.5, such as in the range of 0.5 to 0.75, for example in the range of 0.75 to 1, such as in the range of 1 to 5, for example in the range of 5 to 10, such in the range of 10 to 20, for example in the range of 20 to 30 parts glucose for every part mannose. Preferably the polysaccharides comprise in the range of 0.5 to 2 parts glucose for every part mannose, more preferably 13.4±0.4 parts mannose 12.6±1.3 part glucose.

In a very preferred embodiment of the invention the composition comprises a mixture of polysaccharides comprises the monosacharides galactose, mannose, and glucose in the ratio 1:5 to 25:1 to 50, more preferably 1:13.4±0.4:12.6±1.3.

In another embodiment of the invention the composition comprises a mixture of polysaccharides, wherein the polysaccharides within said mixture having a molecular weight in the range of 50,000 to 100,000 comprises in the range of 3 to 15, preferably in the range of 4 to 14, more preferably in the range of 5 to 13, even more preferably in the range of 6 to 12, yet more preferably in the range of 7 to 11, even more preferably in the range of 7.9 to 9.9, for example approximately 8.9 parts mannose for every part galactose. In this embodiment it is preferred that the polysaccharides having a molecular weight in the range of 50,000 to 100,000 comprises in the range of 1 to 5, preferably in the range of 2 to 4, even more preferably in the range of 2.5 to 3.5, such as approximately 2.9 parts glucose for every part galactose. It is preferred that the polysaccharides of said composition having a molecular weight in the range of 50,000 to 100,000 Da comprise the monosacharides galactose, mannose, and glucose in the ratio 1:4 to 14:1 to 5, preferably the ratio is approximately 1:8.9:2.9.

In another embodiment of the invention the composition comprises a mixture of polysaccharides, wherein the polysaccharides within said mixture having a molecular weight in the range of 100,000 to 300,000 comprises in the range of 3 to 15, preferably in the range of 3 to 14, more preferably in the range of 3 to 13, even more preferably in the range of 3 to 12, yet more preferably in the range of 4 to 11, even more preferably in the range of 5 to 10, yet more preferably in the range of 6.3 to 8.3, for example approximately 7.3 parts mannose for every part galactose. In this embodiment it is preferred that the polysaccharides having a molecular weight in the range of 100,000 to 300,000 comprises in the range of 1 to 5, preferably in the range of 2 to 4, even more preferably in the range of 2.5 to 3.5, such as approximately 2.9 parts glucose for every part galactose. It is preferred that the polysaccharides of said composition having a molecular weight in the range of 50,000 to 100,000 Da comprise the monosacharides galactose, mannose, and glucose in the ratio 1:3 to 13:1 to 5, preferably the ratio is approximately 1:7.3:2.9.

In another embodiment of the invention the composition comprises a mixture of polysaccharides, wherein the polysaccharides within said mixture having a molecular weight in the range of 300,000 to 1,000,000 comprises in the range of 3 to 16, preferably in the range of 5 to 15, more preferably in the range of 5 to 14, even more preferably in the range of 6 to 13, yet more preferably in the range of 7 to 12, even more preferably in the range of 8.9 to 10.9, for example approximately 9.9 parts mannose for every part galactose. In this embodiment it is preferred that the polysaccharides having a molecular weight in the range of 300,000 to 1,000,000 comprises in the range of 1 to 5, preferably in the range of 2 to 4, even more preferably in the range of 2.5 to 3.5, such as approximately 3.1 parts glucose for every part galactose. It is preferred that the polysaccharides of said composition having a molecular weight in the range of 300,000 to 1,000,000 Da comprise the monosacharides galactose, mannose, and glucose in the ratio 1:5 to 15:1 to 5, preferably the ratio is approximately 1:9.9:3.1.

In another embodiment of the invention the composition comprises a mixture of polysaccharides, wherein the polysaccharides within said mixture having a molecular weight of at least 1,000,000 comprises in the range of 3 to 17, preferably in the range of 4 to 16, more preferably in the range of 5 to 15, even more preferably in the range of 6 to 14, yet more preferably in the range of 7 to 13, even more preferably in the range of 8 to 12, even more preferably in the range of 9.3 to 11.3, for example approximately 10.3 parts mannose for every part galactose. In this embodiment it is preferred that the polysaccharides having a molecular weight of at least 1,000,000 comprises in the range of 1 to 5, preferably in the range of 2 to 4, even more preferably in the range of 2.5 to 3.5, such as approximately 2.9 parts glucose for every part galactose. It is preferred that the polysaccharides of said composition having a molecular weight in the range of at least 1,000,000 Da comprise the monosacharides galactose, mannose, and glucose in the ratio 1:4 to 1:5 to 15:1 to 5, preferably the ratio is approximately 1:10.3:2.9.

In one embodiment, the polysaccharides according to the present invention have a molar ratio of galactose:mannose:glucose of 1:10 to 20:30 to 50, such as 1:12 to 18:35 to 45; for example 1:14 to 16:38 to 42, such as 1:about 15:about 40, for example 1:15:40.

Accordingly, in one embodiment a composition the polypeptides comprise the monosaccharides galactose, mannose and glucose in the ratio (galactose:mannose:glucose) of 1:0 to 25:1 to 50, such as 1:10 to 20:30 to 50, such as 1:12 to 18:35 to 45; for example 1:14 to 16:38 to 42, such as 1:about 15:about 40, for example 1:15:40.

In another one embodiment, the polysaccharides according to the present invention have a molar ratio of galactose:mannose:glucose of 1:0.5 to 5:6 to 12, such as 1:1 to 4:7 to 11; for example 1:1.5 to 3.5:7.5 to 10, such as 1:2.0 to 3.0:7.5 to 9.5, for example 1:2.2 to 2.8:8.0 to 9.0, such as 1:about 2.5:8.0 to 9.0, for example 1:2.5:8.0 to 9.0, such as 1:2.5:8.6.

Two preferred embodiments of the composition of the present invention have a molar ratio of galactose:mannose:glucose of 1:12:40 and 1:3:5.

In one preferred embodiment of the present invention, the sugar composition is obtainable from *Agaricus blazei* and comprises 10-20 parts mannose, 30-50 parts glucose and 0-2 parts galactose, such as e.g. 11-17 parts mannose, 35-45 parts glucose and 0-1 parts galactose. More preferably, the sugar composition is obtainable from Agaricus blazei and comprises about 15 parts mannose, about 40 parts glucose and about 1 part galactose, wherein "about" signifies within 20% difference from the stated value, such as within 10% difference from the stated value, such as within 5% difference from the stated value.

In another preferred embodiment of the present invention, the sugar composition is obtainable from *Ganoderma* and comprises 0.5-5 parts mannose, 4-15 parts glucose and 0-2 parts galactose, such as e.g. 2-3 parts mannose, 7-9.5 parts glucose and 0.5-1.5 parts galactose. More preferably, the the sugar composition is obtainable from *Ganoderma* and comprises about 2.5 parts mannose, about 8.6 parts glucose and about 1 part galactose, wherein "about" signifies within 20% difference from the stated value, such as within 10% difference from the stated value, such as within 5% difference from the stated value.

Determination of the monosaccharide content of polysaccharides with a molecular weight within a given range may be determined by fractionating the composition according to size for example by ultrafiltration, microfiltration, ultracentrifugation or gelfiltration. For example this may be done as described in example 2.

It is preferred that the mixture of polysaccharides comprises the monosaccharides galactose, mannose, and glucose in the ratio (0-1.5):(0-0.5) to (15-35):(0.5-1.5) to (45-55), such as e.g. any of the following:
(0-1.5):(0-0.5) to (15-35):(0.5-1.5) to (45-55),
(0.8-1.2):(0-0.5) to (20-30):(0.5-1.5) to (45-55),
(0-1.5):(0-0.1) to (15-35):(0.5-1.5) to (45-55),
(0.8-1.2):(0-0.5) to (15-35):(0.5-1.5) to (45-55),
(0-1.5):(0-0.5) to (20-30):(0.5-1.5) to (48-52),
(0.8-1.2):(0-0.5) to (15-35):(0.5-1.5) to (48-52),
(0-1.5):(0-0.1) to (15-35):(0.5-1.5) to (48-52),
(0.8-1.2):(0-0.1) to (15-35):(0.5-1.5) to (48-52),
(0-1.5):(0-0.5) to (20-30):(0.5-1.5) to (49-51),
(0.8-1.2):(0-0.5) to (15-35):(0.5-1.5) to (49-51),
(0-1.5):(0-0.1) to (15-35):(0.5-1.5) to (49-51),
(0.8-1.2):(0-0.1) to (20-30):(0.5-1.5) to (49-51),
(0-1.5):(0-0.5) to (15-35):(0.5-1.5) to (45-55),
(0.8-1.2):(0-0.5) to (15-35):(0.5-1.5) to (45-55),
(0-1.5):(0-0.5) to (20-30):(0.5-1.5) to (48-52),
(0.8-1.2):(0-0.5) to (15-35):(0.5-1.5) to (48-52),
(0-1.5):(0-0.5) to (15-35):(0.5-1.5) to (49-51),
(0.8-1.2):(0-0.5) to (20-30):(0.5-1.5) to (49-51), In another embodiment of the present invention, the sugar composition of the composition of the present invention comprises 1-25 parts mannose, 5-45 parts glucose and 0-1.5 parts galactose; (by "part" is meant herein the relative molar ratio, i.e. for every 1-25 moles mannose, there are 5-45 moles of glucose and 0-1.5 moles of galactose), thus the sugar composition may comprise A), B) and C), as follows:

A) one quantity of mannose selected from the group consisting of:
1-25 parts
1-20 parts
1-15 parts
1-10 parts
1-4 parts
1-3 parts
1.5-2.5 parts
4-6 parts
7-15 parts
7-23 parts
9-19 parts 12-20 parts
10-25 parts
12-17 parts
14-16 parts and B) one quantity of glucose selected from the group consisting of:
5-45 parts
5-13 parts
7-13 parts
7-15 parts
8-15 parts
8-12 parts
8-10 parts
8-9 parts
8.4-8.7 parts
8.6 parts
10-20 parts
20-30 parts
30-40 parts
30-45 parts
35-45 parts
35-42 parts
37-45 parts
39-41 parts
40 parts and C) one quantity of galactose selected from the group consisting of:
0-1.5 parts
0.2-1.2 parts
0.7-1.5 parts
0-0.2
0-1 parts
0 parts
1 part
1-1.5 parts

PREFERRED EMBODIMENTS OF THE PRESENT INVENTION

In one embodiment of the present invention is provided a composition comprising one or more polypeptides and a mixture of polysaccharides, wherein:

a) the majority of the polysaccharides of the composition have a molecular weight of at least 30,000 Da and wherein said mixture of polysaccharides comprises the monosaccharides galactose, mannose and glucose in the ratio 1:0 to 25:1 to 50, or b) the majority of the polysaccharides of the composition have a molecular weight of at least 100,000 Da and wherein said mixture of polysaccharides comprises the monosaccharides galactose, mannose and glucose in the ratio 0 to 0.5:0.5 to 10:0.5 to 50, or c) the majority of the polysaccharides of the composition have a molecular weight of at least 1,000 Da and wherein said mixture of polysaccharides comprises the monosaccharides galactose, mannose and glucose in the ratio 1:0 to 25:1 to 50.

Thus, in one embodiment of the present invention the majority of the polysaccharides of the composition have a molecular weight of at least 10,000 Da, preferably at least 30,000 Da, and said mixture of polysaccharides comprises the monosaccharides galactose, mannose and glucose in the ratio 1:0 to 25:1 to 50, such as any of the following ratios:
1:0 to 15:1 to 25,
1:15 to 25:1 to 25,
1:0 to 25:25 to 50,
1:15 to 25:25 to 50,
1:0 to 7:1 to 50,
1:0 to 7:1 to 25,
1:7 to 15:1 to 50,
1:7 to 15:40 to 50,
1:0 to 25:1 to 40,
1:0 to 25:25 to 40,
1:0 to 10:1 to 50, In another embodiment of the present invention the majority of the polysaccharides of the composition have a molecular weight of at least 1,000 Da, such as at least 5,000 Da, for example at least 10,000 Da, such as at least 20,000 Da, for example at least 40,000 Da, such as at least 50,000 Da, for example at least 60,000 Da 75,000 Da, for example at least 85,000 Da, most preferably at least 100,000 Da; and said mixture of polysaccharides comprises the monosaccharides galactose, mannose and glucose in the ratio 0 to 0.5:0.5 to 10:0.5 to 50, such as any of the following ratios:
0 to 0.5:0.5 to 7:0.5 to 50
0 to 0.5:0.5 to 4:0.5 to 50
0 to 0.5:0.5 to 2:0.5 to 50
0 to 0.5:3 to 10:0.5 to 50
0 to 0.5:5 to 10:0.5 to 50
0 to 0.5:3 to 7:0.5 to 50
0 to 0.1:0.5 to 7:0.5 to 50
0 to 0.1:0.5 to 4:0.5 to 50
0 to 0.1:0.5 to 2:0.5 to 50
0 to 0.1:3 to 10:0.5 to 50
0 to 0.1:5 to 10:0.5 to 50
0 to 0.1:3 to 7:0.5 to 50
0 to 0.5:0.5 to 7:0.5 to 25
0 to 0.5:0.5 to 4:0.5 to 12
0 to 0.5:0.5 to 2:10 to 50
0 to 0.5:3 to 10:0.5 to 5
0 to 0.5:5 to 10:15 to 40
0 to 0.5:3 to 7:25 to 50
0 to 0.1:0.5 to 7:45 to 50
0 to 0.1:0.5 to 4:40 to 50
0 to 0.1:0.5 to 2:35 to 50
0 to 0.1:3 to 10:20 to 30
0 to 0.1:5 to 10:15 to 45
0 to 0.1:3 to 7:25 to 30
0 to 0.1:0.5 to 1.5:15 to 20
0 to 0.1:0.5 to 1.5:0.5 to 1.5

Preferably, said ratio is about 0:1:18 or about 0:1:1.

In another embodiment of the present invention the majority of the polysaccharides of the composition have a molecular weight of at least 500 Da, such as at least 800 Da, such as at least 1,000 Da, for example at least 5,000 Da, for example at least 10,000 Da, such as at least 20,000 Da, for example at least 40,000 Da, such as at least 50,000 Da, for example at least 60,000 Da 75,000 Da, for example at least 85,000 Da, such as at least 100,000 Da, most preferably at least 1,000 Da; and said mixture of polysaccharides comprises the monosaccharides galactose, mannose and glucose in the ratio 1:0 to 25:1 to 50, such as any of the following ratios:
1:0 to 25:1 to 50
1:0 to 20:1 to 50
1:0 to 15:1 to 50
1:0 to 10:1 to 50
1:0 to 5:1 to 50
1:10 to 25:1 to 50
1:10 to 15:1 to 50
1:15 to 25:1 to 50
1:17 to 25:1 to 50
1:10 to 18:1 to 50

1:0 to 25:1 to 45
1:0 to 25:1 to 40
1:0 to 25:1 to 35
1:0 to 25:1 to 30
1:0 to 25:1 to 20
1:0 to 25:1 to 15
1:0 to 25:1 to 5
1:0 to 25:10 to 20
1:0 to 25:10 to 30
1:0 to 25:10 to 40
1:0 to 25:20 to 50
1:0 to 25:20 to 30
1:0 to 25:20 to 40
1:0 to 25:30 to 50
1:0 to 25:30 to 40
1:0 to 25:30 to 35
1:0 to 25:35 to 40
1:0 to 25:1 to 45
1:0 to 20:1 to 40
1:0 to 15:1 to 35
1:0 to 10:1 to 30
1:0 to 5:1 to 20
1:10 to 25:1 to 15
1:10 to 15:10 to 50
1:15 to 25:10 to 40
1:17 to 25:1 to 50
1:10 to 18:1 to 50
1:8 to 15:30 to 50
1:11 to 13:35 to 45
1:11 to 13:38 to 42
1:1 to 5:3 to 9
1:2 to 4:4 to 6

Preferably, said ratio is about 1:12:40 or about 1:3:5.

Polypeptide

The composition according to the invention preferably comprises polypeptides. The term polypeptide as used herein covers both proteins, peptides and polypeptides. Said polypeptides may be in free form, they may be covalently linked to a polysaccharide or they may be non-covalently associated with a polysaccharide or a mixture of the aforementioned.

It is preferred that the composition comprises sufficient polypeptide in order to allow for oral administration of the composition. If the composition comprises too little polypeptide, then no or little immune modulation is obtained in an individual after oral administration of the composition to said individual. It is therefore preferred that the composition of the invention comprises at least 10 µg/L, more preferably at least 20 µ/L, even more preferably at least 25 µg/L, for example in the range of 10 to 1000 µg/L, such as in the range of 20 to 1000 µg/L, for example in the range of 25 to 1000 µg/L, such as in the range of 25 to 100 µg/L, for example in the range of 25 to 35 µg/L polypeptide, preferably soluble polypeptide. It is preferred that the composition comprising the aforementioned concentration of polypeptide, comprises in the range of 0.1 to 2, more preferably in the range of 0.5 to 1.5, even more preferably around 1 mg/ml polysaccharide. If the composition comprises more or less polysaccharide it is preferred that the amount of polypeptide is proportionally reduced or enhanced.

Method of Preparing the Composition

Preferably, the compositions of the invention are prepared by a method comprising the steps of
  i) Cultivating a fungus in a liquid growth medium
  ii) Purifying said composition from said liquid growth medium Cultivating the fungus in a liquid growth medium in general involves dissolving nutrient compounds required for growth of said fungus in water, transferring the solution to a bioreactor and inoculating the bioreactor with cells or spores of the fungus, such as a fungal mycelium, or fractions thereof, to be cultivated. This is done under sterile conditions and with control of the environment in order to give the fungus a suitable chemical and physical environment. Cultivating fungi in liquid growth medium is also termed "liquid state" cultivation.

During "liquid-state" cultivation the medium with the fungal biomass is preferably agitated to reduce the occurrence of gradients and to ensure oxygen availability to the submerged cells. When fungi are grown in a bioreactor, oxygen may be supplied to the liquid medium and the level of dissolved oxygen may be controlled by known methods.

The liquid growth medium is an aqueous solution, preferably sterile water, comprising nutrient compounds. The liquid medium supports fungal growth and preferably stimulates the production of extracellular compounds, such as immune modulating agents. The liquid growth medium may comprise one or more typical ingredients required for growth of microbial organisms such as malt extract, yeast extract, peptone, glucose, sucrose, sucrose, salts providing phosphate, magnesium and potassium, corn-steep liquor and vitamins such as thiamine. More preferably, the medium comprises sucrose, corns steep liquor, phosphate and magnesium for mycelium growth and production of polysaccharides.

For inoculation of the growth medium, fungal mycelium, such as *Lentinus edodes* mycelium from agar plates containing for example malt extract, yeast extract, peptone and glucose can be used. Fungi can initially be cultivated on agar plates comprising the above nutrient compounds supporting the growth of the fungus. The plates are inoculated with mycelium and incubated at least until a visible growth is evident on the plates. Dependent on the fungus, this usually can take from about 7 days to about 24 days or from about 10 to 30 days, typically 14 days or up to 20 days, at a temperature in the range of from 18 to 32° C., preferably in the area of from 22 to 30° C., such as a temperature of about 23° C. to 27° C., such as around 25° C.

As an alternative to inoculation with mycelium from agar plates, inoculation of the growth medium can be carried out by using mycelium from a fermentation broth in e.g. a shake flask medium comprising nutrient compounds supporting cell growth. Shake flasks for cultivating fungal mycelium can initially be inoculated with the mycelium which is cultivated on agar plates. The mycelium is taken from the plates and transferred aseptically to shake flasks containing sterile water comprising dissolved nutrient compounds and nutrient salts supporting the growth of the fungal mycelium. A typical growth medium contains sucrose, corn steep liquor, phosphate and a magnesium. The amount of inoculation material which gives the highest production of extracellular lentinan can be selected following initial experiments.

The time for incubation of the shake flasks depends on the specific fungus. Typically, the shake flasks can be incubated by shaking for 6 to 21 days, preferably from 7 to 18 days, more preferably from 8 to 14 days at a temperature in the range of from 18 to 32° C., preferably in the area of from 22 to 30° C., such as a temperature of about 23° C., for example 24° C., such as 25° C., for example 26° C., such as 27° C., for example 28° C., such as 29° C., for example 30° C. The shake flasks may also be incubated from 8-25 days, more preferably from 10-20 days, more preferably from 12-18 days. The temperature may also be from 18 to 37° C., preferably from 23 to 32° C. such as about 25° C.

The content of the shake flasks can be used for inoculating a bioreactor. In that case, the reactor comprises a sterile solution of nutrient compounds and nutrient salts in water for mono-culture cultivation of basidiomycete fungal mycelium, or fractions thereof, such as *Lentinus* fungal mycelium, such as *Lentinus edodes*.

The bioreactor fermentation period is typically in the range of from 50 hours to 300 hours, preferably in the range of from 80 hours to 270 hours, and the temperature is kept constant in the range of 18 to 32° C., preferably in the area of from 22 to 31° C., such as a temperature of about 23° C., for example 24° C., such as 25° C., for example 26° C., such as 27° C., for example 28° C., such as 29° C., for example 30° C. The temperature may also be from 18 to 37° C., preferably from 23 to 32° C. such as about 25° C.

The reactor is fitted with an inlet for supplying air to the fermentation broth, and the fermentation broth is preferably kept under continuous agitation either as a result of the addition of air, or by means of a mixer device suitable for providing a good mixing of the content of the reactor.

It is preferred to adjust the pH of the growth medium to from about 3 to about 7, such as a pH of from about 4.5 to about 6.5, for example a pH of about 6, before the growth medium is inoculated with fungal mycelium, or fractions thereof, such as *L. edodes* mycelium. After the initial adjustment, pH may be dropped naturally during the course of the fermentation, or controlled at a particular value in the range pH 3 to 7, using addition of suitable pH-control agents, such as acid and base. The temperature of the growth medium is preferably in the range of from 18 to 32° C., preferably in the area of from 22 to 31° C., such as a temperature of about 23° C., for example 24° C., such as 25° C., for example 26° C., such as 27° C., for example 28° C., such as 29° C., for example 30° C. The temperature may also be from 18 to 37° C., preferably from 23 to 32° C. such as about 25° C.

Samples can be obtained from the bioreactor and analysed for biomass, metabolic products and nutrient compounds, the determinations of which can assist the operator of the bioreactor in the running of the fermentation process. Typical analyses routinely carried out are determination of biomass, residual sugar concentration and extracellular polysaccharide concentration. A person skilled in the art knows the methods for analysis which can be employed in this respect.

Preferably, the method for preparing the compositions according to the invention involves a step of purifying the extracellular fraction of the liquid growth medium from the fungal mycelium. The extracellular fraction of the liquid fermentation medium is also termed the supernatant and this fraction can be separated from the fungal mycelium by e.g. centrifugation or filtration, or indeed by any other means available for obtaining a liquid fraction essentially without any fungal mycelium present therein. The term "essentially without any fungal mycelium present therein" shall denote that the concentration of fungal mycelium, including fractions thereof, has been reduced at least by a factor of $10^3$, such as reduced by a factor of at least $10^4$, for example a factor of at least $10^5$, such as reduced by a factor of at least $10^6$.

In preferred embodiments of the invention the purification comprises at least one size fractionation step. Preferably, this size fractionation step is performed on the extracellular fraction. This size fractionation step may ensure that every polysaccharide of the composition has a molecular weight of at least a given value (see also herein above). The size fractionation step may be any size fraction known to the skilled person, for example ultracentrifugation, ultrafiltration, microfiltration or gelfiltration. Thus in a preferred embodiment of the invention, the composition is purified from a liquid growth medium by a method involving one or more purification steps selected from the group consisting of ultracentrifugation, ultrafiltration, microfiltration and gelfiltration. Preferably, the purification step(s) are selected from the group consisting of ultrafiltration, microfiltration and ultracentrifucation, even more preferably from the group consisting of ultrafiltration and microfiltration.

Ultrafiltration is a membrane process where the membrane fractionates components of a liquid according to size. The membrane configuration is normally cross-flow wherein the liquid containing the relevant components are flowing across the membrane. Some of the liquid, containing components smaller than the nominal pore size of the membrane will permeate through the membrane. Molecules larger than the nominal pore size will be retained. The desired product may be in the retentate or the filtrate. If the ultrafiltration is performed in order to prepare a composition, wherein every polysaccharide within said composition has a molecular weight above a given value, the desired product is in the retentate. If a serial fractionation is made, the product may be in the retentate or filtrate.

Microfiltration is a membrane separation process similar to UF but with even larger membrane pore size allowing larger particles to pass through.

Gel filtration is a chromatographic technique in which particles are separated according to size. The filtration medium will typically be small gel beads which will take up the molecules that can pass through the bead pores. Larger molecules will pass through the column without being taken up by the beads.

Gel-filtration, ultrafiltration or microfiltration may for example be performed as described in R Hatti-Kaul and B Mattiasson (2001), *Downstream Processing in Biotechnology*, in Basic Biotechnology, eds C Ratledge and B Kristiansen, Cambridge University Press) pp 189.

Non-limiting methods of preparing the compositions according to the invention are described in e.g. examples 1, 7 and 8.

Methods of purifying extracellular agents from a liquid growth medium involving alcohol precipitation have been described. However, alcohol precipitation may reduce the immune modulating effect and compositions purified using alcohol precipitation are therefore less preferable. In one embodiment of the invention the method therefore does not involve an alcohol precipitation step, more preferably the method does not involve a precipitation step.

Pharmaceutical Compositions and Uses Thereof

Provided in another embodiment of the invention is the use of the compositions of the invention in a method for stimulating the immune system of an individual in need of such stimulation. The composition may be administered e.g. orally or subcutaneously to the individual in a pharmaceutically effective amount capable of stimulating the immune system of the individual. The stimulation of the immune system can be demonstrated by e.g. increased antibody production, by activation of helper T-cells, or by increased production of interleukins such as Interleukin 1 and Interleukin 2.

Provided in yet another embodiment of the invention is the use of the compositions of the invention in the manufacture of a medicament for treating an immune compromised condition in an individual in need of such treatment. An immune compromised condition in an individual may be demonstrated e.g. by immune system factors such as an insufficient amount of antibodies, or a decreased antibody production, by an insufficient amount of helper T-cells, or a decreased production of helper T-cells in the individual, by an insufficient amount of B-cells, or a decreased production of B-cells in the individual, by an insufficient amount of natural killer (NK)-cells, or by a decreased production of NK.cells in an individual or by an insufficient amount of interleukins such as Interleukin 1 and Interleukin 2, or a decreased production of interleukins such as Interleukin 1 and Interleukin 2 in the individual. The immune compromised condition may be any of those disclosed below. The treatment may be prophylactic, ameliorating or curative.

"Insufficient amount" and "decreased production" as used herein above shall denote such amounts and productions which a medical expert considers as being below a predetermined level or value normally associated with a healthy individual. The amount and/or production will generally depend on factors such as age, general physical condition, and the like. For this reason a predetermined level or value shall be determined on an individual basis by a medical expert. One indication of an immune compromised condition in an individual is a gradually decreasing number of antibodies, a gradually decreasing number of CD4 (positive) cells, or a gradually decreasing number of T-helper cells per unit (blood) sample volume measured over time, such as days, weeks, months or years.

In one aspect the present invention relates to pharmaceutical compositions comprising the composition according to the invention and pharmaceutically acceptable carrier(s). The pharmaceutical compositions may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, lozenges, powders, syrups, solutions or suspensions.

In one aspect the invention relates to a method of treatment of an individual diagnosed with an immune compromised condition, said method comprising the steps of administering to said individual the composition according to the invention or the pharmaceutical composition according to the invention in an amount effective in treating said immune compromised condition.

The administered amount may in be an amount effective in prophylactically treating said immune compromised condition.

Also provided is a method of treatment of an individual recovering from surgery or illness and at risk of contracting an immune compromised condition, said method comprising the steps of administering to said individual the composition according to the invention or the pharmaceutical composition according to the invention in an amount effective in boosting the immune system of said individual.

Furthermore a method of treatment of an individual diagnosed with or at risk of contracting acquired immunodeficiency syndrome is provided, said method comprising the steps of administering to said individual the composition according to the invention or the pharmaceutical composition according to the invention in an amount effective in treating or prophylactically treating said syndrome.

The immune compromised condition may be selected from the group consisting of an infectious disease, a parasitic disease, haemophilus meningitis, pneumococcal meningitis, streptococcal meningitis, staphylococcal meningitis, meningitis due to other organisms, encephalitis, viral pneumonia, pneumococcal pneumonia, other bacterial pneumonia, pneumonia due to other specified organisms except bacteria, bronchopneumonia, organism unspecific pneumonia, influenza, unspecified diarrhea, hepatitis unspecified, acute and subacute necrosis of the liver, chronic hepatitis, and abscess of liver.

Furthermore, the immune compromised condition may be an infectious or parasitic disease caused by, or selected from, *cholera, salmonella*, shigellosis, *Escherichia coli*, intestinal infection due to other specified bacteria, *Clostridium difficile*, viral gastroenteritis, infectious colitis, enteritis and gastroenteritis, infectious diarrhea, tuberculosis, listeriosis, pasteurellosis, *mycobacterium, diphtheria, pertussis,* meningococcus, *streptococcus* septicaemia, *staphylococcus* septicaemia, pneumococcal septicaemia, septicaemia due to anaerobes, septicaemia due to other gram-negative organisms, actinomycotic infection, gas gangrene, toxic shock syndrome, necrotizing faciitis, Friedlander's *bacillus, haemophilus influenzae, pseudomonas*, AIDS/HIV infections, acute poliomyelitis, Creutzfeldt-Jacob disease, subacute sclerosing panencephalitis, progressive multifocal leucoencephalopathy, unspecified slow virus infection of the central nervous system, coxsackie virus, unspecified viral meningitis, lymphocytic choriomeningitis, unspecified viral encephalitis, chickenpox, herpes zoster, herpes simplex, viral hepatitis 'A', viral hepatitis 'B', other specified viral hepatitis, chronic hepatitis, abscess/acute necrosis of liver, infectious mononucleosis, cytomegalic inclusion disease, chlamydiae, adenovirus, viral infection, syphilis, *candida*, unspecified histoplasmosis, aspergillosis, cryptococcosis, mycoses, strongyloidiasis, intestinal parasitism, toxoplasmosis, sarcoidosis, pneumocystis carinii, post polio syndrome, *haemophilus* meningitis, pneumococcal meningitis, *streptococcal* meningitis, *staphylococcal* meningitis, encephalitis, pneumonia due to adenovirus, pneumonia due to respiratory syncytial virus, pneumonia due to parainfluenza virus, pneumonia due to other virus, viral pneumonia, pneumococcal pneumonia, pneumonia due to *klebsiella pneumoniae*, pneumonia due to *pseudomonas*, pneumonia due to *haemophilus influenzae*, pneumonia due to *streptococcus*, pneumonia due to *staphylococcus*, and bacterial pneumonia.

The individual may be a mammal, such as a human being.

The compositions of the invention may be administered using any suitable administration form; usually however, administration will be oral or parenteral. Oral administration in the form of a syrup comprising the composition and/or a capsule containing a syrup comprising the composition or in a powder form of the composition is preferred.

The dosage requirements will vary with the particular composition employed, the route of administration and the particular individual being treated. Ideally, an individual to be treated by the present method will receive a pharmaceutically effective amount of the compound in the maximum tolerated dose.

In general the daily oral dosage regimen may be about 0.001 to about 100 mg/kg, preferably in the range of 0.01 to 50 mg/kg, more preferably in the range of 0.1 to 10, even more preferably in the range of 1 to 2 mg/kg of total body weight. It will also be recognised by one skilled in the art that the optimal quantity and spacing of individual dosages of the composition will be determined by the nature and extent of the condition being treated, the form, route and site of administration, and the particular patient being treated, and that such optimums can be determined by conventional techniques. It will also be appreciated by one skilled in the art that the optimal course of treatment, i.e., the number of doses of the composition given per day for a defined number of days, can be ascertained by those skilled in the art using conventional course of treatment determination tests.

The composition and the pharmaceutical compositions according to the invention may also form part of a kit comprising said compositions and a dosage regime instruction with guidelines for dose and time administration.

Functional Food

In one embodiment of the present invention, the composition of the present invention is used in the manufacture of a functional food, thus in one embodiment of the present invention, any of the compositions described herein may be comprised in a functional food or nutrition supplement, preferably suitable for human beings. Said functional food is preferably a survival enhancing, longevity enhancing, health enhancing and/or a modulator of a microbial population. More preferably, said functional food is health enhancing and/or a modulator of a microbial population. It is preferred that the functional food is suitable for at least weekly oral intake, such as for daily oral intake. Alternatively, said functional food product may be suitable for use in parenteral or enteral nutrition, preferably in combination with formulations comprising other nutrients known to one skilled in the art.

Products according to the invention may be used for promoting health of human beings, for example for maintaining, strengthening or promoting bone or cardiovascular health. In one preferred embodiment of the present invention, the functional food can be used for the prevention or reduction of osteoporosis. In another preferred embodiment of the present invention, regular consumption of said functional food, such as for example once a day, twice a day, or three times a day, leads to a reduction of the risk of diseases such as colds, coughs and reduces tiredness and fatigue.

While the method of administration or consumption may vary, the functional food is preferably ingested by a human as an ingredient of his or her daily diet. Any of the compositions described herein can be combined with a liquid vehicle, such as water, milk, vegetable oil, juice and the like, or with an ingestible solid or semi-solid foodstuff. For example,they may be mixed into foods such as milk shakes, milk shake mixes, breakfast drinks, juices, flavored drinks, flavored drink mixes, yogurts, puddings, ice creams, ice milks, frostings, frozen yogurts, cheesecake fillings, candy bars, including "health bars" such as granola and fruit bars, gums, hard candy, mayonnaise, pastry fillings such as fruit fillings or cream fillings, cereals, breads, stuffings, dressings and instant potato mixes. The present invention thus relates to a method of producing a functional food composition, comprising mixing any of the compositions described herein (for example obtained from *Lentinus* fungus) with a foodstuff.

For example, said functional food product may be selected from the group of meal replacers, dietary supplements, ice-cream, sauces, dressing, spreads, bars, sweets, snacks, cereals and beverages.

In another preferred embodiment, said functional food is dietary supplement, preferably suitable for ingestion in pill, capsule, tablet or liquid form.

In one embodiment, products according to the invention are prepared whereby any of the compocsitions described herein (such as from Lentinus) is added to the food product such that the level of the composition is between 5 to 5000 mg per 100 g product.

Dairy Product

In one preferred embodiment of the present invention, the functional food is a dairy product. Thus, said functional food may for example be selected from any of the following:

cultured dairy products, yogurts, cottage cheese, cream cheese, dairy dips, sour cream, milkshakes, Butter, Margarine, Low-fat spreads, Cheese, Cottage cheese, Cheese spread, Cheese "strings" for children. Cheese slices, yoghurt, Yoghurt-based carbonated drinks, drinkable yoghurts, low-fat yoghurts, refrigerated dips, sour cream, Ice cream, Cream, Low-fat cream-replacement, Fermented milk such as kefir.

In one preferred embodiment of the present invention, said dairy product is a cheese-based product, such as selected from low-fat cheese, hard cheese, soft cheese, coftage cheese, cheese spread, cheese "strings" for children or cheese slices suitable for sandwiches.

In another preferred embodiment of the present invention, said dairy product is a yoghurt-based product, such as selected from a set yoghurt, a runny or pourable yoghurt, a yoghurt-based carbonated drink, a drinking or drinkable yoghurt, a low-fat yoghurt. Said yoghurt-based product may for example be fermented with *Lactobacillus bulgaricus* and/or *Streptococcus thermophilus*.

In another preferred embodiment of the present invention, said dairy product is a cultured dairy product, such as a cultured fluid (for example drinkable yogurt/yogurt smoothies, kefir, probiotic shots); a non-drinkable yogurt (for example in a cup or tubes); and/or another non-pourable cultured dairy product (for example cottage cheese, cream cheese, dairy dips or sour cream).

In another preferred embodiment of the present invention, said dairy product is another type of dairy product, such as selected from the group consisting of: refrigerated dips and sour cream, ice cream, cream, low-fat cream-replacement, fermented milk such as kefir, fermented beverages, such as drinkable yoghurt and kefir.

Health Drink

In another preferred embodiment of the present invention, the functional food according to the present invention is a health drink. Said health drink is in one embodiment fruit juice-based, which may be concentrated as a "squash", to be diluted to taste. Said fruit juice or squash preferably comprises concentrated fruit juice. Preferred fruit juices include, but are not restricted to, citrus fruit juices such as orange, grapefruit, lemon or lime, or combinations thereof. In another preferred embodiment, said fruit juice or squash comprises (preferably concentrated) berry juice(s), such as from raspberries, strawberries, blackberries, loganberries, cranberries, redcurrants, blackcurrants, blueberries, or combinations thereof, and/or combinations with citrus fruit juices. In another preferred embodiment, said fruit juice or squash comprises juice(s) from one or more of Pineapple, Passion Fruit, Mango, apple, pear, apricot, Pomegranate, guava, tomato and/or combinations with any other types of fruit juices. Preferred juice bases are selected from the following group:

Apple
Apricots
Banana
Blackberries
Blueberries
Carambola (Starfruit)
cherries
Dates
Figs
fruit cocktail
grape
grapefruit
Kiwi Fruit
Lemons
Mandarin Orange
Mangos
melon
Nectarines
Orange Papaya
Peaches
Pear
Pineapple
Plantain
Plum
Raspberries
strawberries
Tangerines
watermelon or combinations thereof.

Further preferred juice bases are selected from the following group:
Apple
Carrot
Cranberry
Grape
Grapefruit (pink or white)
Lemon
Lime
Orange
Pineapple
Pineapple
Prune
Tangerine
Tomato or combinations thereof.

Said health drink may also be water-based, such as a mineral water-based product, such as flavored mineral water-based products. Said flavoring is preferably from fruit juices and/or other natural products.

In one preferred embodiment of the present invention, said health drink is an energy shot comprising sugars and other energy-providing products, such as comprised in an 25 or 30 cl bottle.

In another preferred embodiment of the present invention, said health drink is an alcoholic beverage, such as a dairy-based alcoholic beverage.

In another preferred embodiment of the present invention, said health drink is a meal replacement drinks.

It is envisaged that the health drink of the present invention may also be manufactured as a concentrate or premix, ready for making up to the drink at a later stage, preferably by the consumer.

Solid Functional Food

In one preferred embodiment of the present invention, the functional food is a solid functional food, such as selected from the group consisting of: Biscuits/crackers, breakfast cereal, soup, muesli, Chewing gum, Sweets (such as boiled sweets), fresh bakery products (fresh bread, cakes, muffins, waffles etc.), dry bakery products (crispbread, biscuits, crackers etc.), cereal products (breakfast cereals, fibre and sterol enriched flours, mueslis, cereal based and muesli bars, such bars possibly containing chocolate, pasta products, snacks etc.), bran products (granulated and/or toasted bran products, flavored and/or sterol coated bran products and bran-bran mixes etc.).

In another preferred embodiment of the present invention, said solid functional food is a ready mix (preferably in powder form), either for baking (e.g. breads, cakes, muffins, waffles, pizzas, pancakes) or for cooking (e.g. soups, sauces, desserts, puddings) to be used in preparing or manufacturing of foods In another preferred embodiment of the present invention, said solid functional food is a meat product (sausages, meatballs, cold cuts etc.)

In another preferred embodiment of the present invention, said solid functional food is a bread or morning product/bakery snack. Thus, said bread may be white, brown or wholemeal bread. In another preferred embodiment of the present invention, said bread may be selected from the following bread types: malted wheats, milk breads, bran-enriched and mixed grain breads. The bread may be any shape, such as e.g. cob, coburg, cottage, cholla, bloomer, barrel, batch, sandwich, tin, vienna or farmhouse. In one preferred embodiment of the present invention, said bread is selected from any of the following bread types:
Wholemeal bread
Brown bread
Wheatgerm bread (bread containing added processed wheatgerm of no less than 10%)
Softgrain bread (made from white flour with additional grains of softened rye and wheat to increase the fibre content (preferably by 30%) compared with conventional white bread)
Granary breads
Malt breads In another preferred embodiment of the present invention, said bread is selected from any of the following bread types:
Ciabatta
pitta
naan
cholla
Focaccia
Soda Bread or brown soda bread (made using wholemeal flour)
rye breads
baguette or French stick
croissants
bagel In another preferred embodiment of the present invention, said bread is a flat bread, such as selected from any of the following bread types: Chapattis, Paratas and Roti, Mexican tortilla, flat "wrap" or flour tortilla, pancakes.

In another preferred embodiment of the present invention, the functional food is a morning snack or bakery product. Said bakery product may be either sweet or savoury, for example savoury.

Preferred bakery products include, but are not restricted to: rolls and baps, toasting products such as muffins, crumpets and pikelets, scones, teacakes, buns and other fruited products, hot plate products such as pancakes and griddle scones, waffles and potato cakes, hot cross buns. croissants, brioches, pain-au-chocolat, bagels, American sweet muffins and other semi-sweet bread products.

Vegetable Oil-Based Product

In another preferred embodiment of the present invention, the functional food is a vegetable oil-based product (spreads, salad oils, mayonnaise etc.)

Frozen Confectionery Products

In another preferred embodiment of the present invention, the functional food is a frozen confectionary product. For the purpose of the invention the term frozen confectionery product includes milk containing frozen confections such as ice-cream, frozen yoghurt, sherbet, sorbet, ice milk and frozen custard, water-ices, granitas and frozen fruit purees.

Preferably the level of solids in the frozen confection (e.g. sugar, fat, flavoring etc) is more than 3 wt %, more preferred from 10 to 70 wt %, for example 40 to 70 wt %.

Ice-cream will typically comprise 2 to 20 wt % of fat, 0 to 20 wt % of sweeteners, 2 to 20 wt % of non-fat milk components and optional components such as emulsifiers, stabilisers, preservatives, flavouring ingredients, vitamins, minerals, etc, the balance being water. Typically ice-cream will be aerated e.g. to an overrun of 20 to 400%, more general 40 to 200% and frozen to a temperature of from −2 to −200 degrees. C., more general −10 to −30 degrees C. Ice-cream normally comprises calcium at a level of about 0.1 wt %.

A typical size of an average serving of frozen confectionery material is 66 g. The composition according to the present invention may be encapsulated or combined with emulsifiers, detergents or other agents to ensure solubilisation and stabilisation of the substance in the product.

Meal Replacers

In another preferred embodiment of the present invention, the functional food is a meal replacer. Meal replacer drinks are typically based on a liquid base which may for example be thickened by means of gums or fibers and whereto a cocktail of minerals and vitamins are added. The drink can be flavored to the desired taste e.g. fruit or choco flavor. A typical serving size may be 330 ml or 330 g. The composition according to the present invention may be encapsulated or combined with emulsifiers, detergents or other agents to ensure solubilisation and stabilisation of the substance in the beverage.

Meal replacer snacks or bars often comprise a matrix of edible material wherein the composition according to the present invention can be incorporated. For example the matrix may be fat based (e.g. couverture or chocolate) or may be based on bakery products (bread, dough, cookies etc) or may be based on agglomerated particles (rice, grain, nuts, raisins, fruit particles). A typical size for a snack or meal replacement bar could be 20-200 g, generally from 40 to 100 g. Further ingredients may be added to the product e.g. flavoring materials, vitamins, minerals etc.

Combinations

In one aspect of the present invention, the functional food comprises a composition according to the present invention in combination with another survival enhancing agent, longevity enhancing agent, health enhancing agent and/or a modulator of a microbial population.

For example, one preferred embodiment of said functional food is a food comprising one or more of the compositions according to the present invention and a probiotic, such as in a probiotic "shot". Another preferred embodiment of the functional food is a food comprising the compounds according to the present invention and a prebiotic, such as in a prebiotic "shot". Another preferred embodiment of the functional food is a food comprising the compositions according to the present invention and a symbiotic, such as in a symbiotic "shot". In one preferred embodiment of the present invention, preferred bacteria for use in the above-mentioned shots are any of the following: *Lactobacillus* sp., such as *L. acidophilus, L. casei, L. fermentum, L. johnsonii, L. lactis, L. plantarum, L. reuteri, L. rhamnosus* and/or *L. salivarius*. In another preferred embodiment of the present invention, preferred bacteria for use in the above-mentioned shots are any of the following: *Bifidobacterium* sp., such as *B. bifidium, B. breve, B. lactis,* and/or *B. longum*. In another preferred embodiment of the present invention, preferred bacteria for use in the above-mentioned shots are any of the following: *Enterococcus faecalis. Escherichia coli, Saccharomyces boulardii, Saccharomyces cerevisiae* and/or *Streptococcus thermophilus*.

The composition according to the present invention may be also combined with other ingredients in a dietary supplement, such as e.g. botanical supplements and/or in a vitamin E capsules, or in a selenium pill. Further preferred combination in said dietary supplements may be with e.g. one or more of the following: antioxidant(s), vitamin C, vitamin E, beta-carotene The functional food of the invention can further encompass other healthy components such as for example vitamins A, B, C, D, E, minerals such as calcium, potassium, magnesium, iron, copper, zinc, selenium and anti-oxidants such as tocopherols, polyphenols. For example, the functional food may comprise a composition according to the invention (such as lentinan) together with vitamin C, the combination capable of causing a reduction in colds and flu in the individual ingesting said functional food.

In a preferred embodiment, compositions of the invention may comprise further ingredients which are believed to reduce or prevent osteoporosis. Examples of such ingredients are calcium, vitamin D, magnesium etc.

Preferred embodiments of suitable functional foods of the invention are described herein below:

Beverage comprising any of the compositions described herein in an amount of 0.1-5%, preferably 0.5-1%.

Fresh bakery product comprising any of the compositions described herein in an amount of 0.9-16%, preferably 2.4-10%, and more preferably 3-5%.

Dry bakery product comprising any of the compositions described herein in an amount of 1.0-20%, preferably 3.2-15% and more preferably 4.4-10%

Cereal product comprising any of the compositions described herein in an amount of 0.8-20%, preferably 1.6-16%, more preferably 2-10%

Bran product comprising any of the compositions described herein in an amount of 4%-25%, preferably 6-20%

Dairy or non-dairy product (e.g. fermented cereal product) comprising any of the compositions described herein in an amount of 0.1-20%, preferably 0.8-8%

Vegetable oil based product comprising any of the compositions described herein in an amount of 0.6-16%, preferably 2.6-10%, more preferably 2.6-5%

Meat product comprising any of the compositions described herein in an amount of 0.1-16%, preferably 0.2-5%.

Dairy product comprising: any of the compositions described herein in an amount of 0.1-16%, preferably 0.2-5%.

Thus, in one embodiment, the present invention is concerned with use of any of the compositions described herein in the manufacture of a functional food, such as any of the functional foods described herein.

EXAMPLES

The following examples describe illustrative embodiments of the invention and should not be regarded as limiting for the invention.

Example 1

Carbohydrate Composition

*Lentinus edodes* was cultivated in liquid culture in medium comprising 15 g/l glucose, 3 g/l malt extract, 3 g/l yeast extract and 5 g/l peptone in shake flasks at 25° C. After cultivation the biomass was separated from the rest of the fermentation broth by filtration. The supernatant was subjected to ultrafiltration using a membrane with a nominal pore size of 50,000 Da. The retentate (herein designated the "MediMush product") was used for analysis of monosaccharide content.

For comparison, commercially available Lentinan for injection (Eureka Bio-Chemicals Pty, Little Collins Street. Melbourne 3000, Australia) was used in a reference experiment performed in parallel (herein after this product is designated "Eureka").

Samples were hydrolysed to their constituent monosaccharides in 1N HCl at 100° C. The hydrolysates were analysed by HPLC using a Dionex MA-1 column with 600 mM NaOH as the mobile phase; detection was by pulsed amperometry.

The major monosaccharides of the MediMush product was mannose and glucose and some galactose. Table A displays the relative monosaccharide content of the MediMush product and Eureka.

TABLE A

| SAMPLE | MANNOSE | GLUCOSE | GALACTOSE |
|---|---|---|---|
| MediMush | 13.4 ± 0.4 | 12.6 ± 1.3 | 1 |
| Eureka | 2.8 | 90.1 | 1 |

Example 2

Molecular Weight Fractionation

For molecular weight characterisation of their biological activity, the MediMush sample was centrifuged through Microsep (Pall Life Sciences) centrifugal ultrafilters at 6° C. and 7,500×g. Filters with nominal MWCO values of 50,000-1,000,000 were used. Analytical results (see table 2) showed that material yielding mannose, glucose and galactose on acid hydrolysis passed through all four MWCO membranes used:

TABLE 2

| MWCO | MANNOSE | GLUCOSE | GALACTOSE |
|---|---|---|---|
| 1000000 | 10.3 | 2.9 | 1 |
| 300000 | 9.9 | 3.1 | 1 |
| 100000 | 7.3 | 2.9 | 1 |
| 50000 | 8.9 | 2.9 | 1 |

Example 3

Soluble Protein

Soluble protein in the samples was measured by a microscale version of the Coomassie dye-binding assay (Mousdale, D. M, Campbell, M. S., Coggins, J. R. "Purification and characterisation of bifunctional dehydroquinase-shikimate: NADP dehydrogenase from pea seedlings". Phytochemistry 367, 217-222 (1987). The amounts of soluble protein in the two products are shown below:

| SAMPLE | SOLUBLE PROTEIN (µg/L) |
|---|---|
| MediMush sample | 31.5 +/− 3.43 |
| Eureka product | 4.5 (+/−0.6, n = 3) |

Example 4

Immunostimulation

Tissue Culture

P388 cells are mouse macrophage like cells, which secrete large amounts of interleukin-1 (IL-1) when stimulated (detailed information on the cells is available from the ECACC). The amount of IL-1 secreted can be quantified using an ELISA (Enzyme-Linked ImmunoabSorbant Assay) based method and used as a measure of how stimulated the cells are. It should be noted that no absolute value exist to calibrate such an assay and it is therefore preferred that a reference sample is analysed in parallel and the IL1 production is evaluated as compared to the IL1 production induced by the reference sample. There are two forms of IL-1, IL1-α and IL-β. The P388 cells are seeded in a 12 well culture plate and allowed to grow overnight. The various stimulants are added at differing concentrations and incubated at 37° C. for 24 hr.

ELISA

50 µl of the stimulated culture medium from each well was mixed with coating buffer and aliquoted into a 96 well ELISA plate and allowed to coat overnight a 4° C. This step allows the antigen (IL-1) to bind to the surface of the ELISA plate. The IL-1 is detected using two antibodies against the two different forms of IL-1, which are raised in a goat (primary antibodies). The next step uses another antibody, which detects the goat antibody (secondary antibody). The antibody is conjugated to horse-radish perioxidase, which gives a colour reaction when substrate is added. The amount of colour measured by a spectrophotometer (ELISA reader) correlates with the amount of IL-1 present thus quantifying how stimulated the tissue culture cells are.

Results

Total Sample Assay.

The two products were tested at a range of concentrations, the optimum value was found to be 50 µg/ml for IL1α and 100 µg/ml for IL1β. Results are given in table 3.

TABLE 3

| Sample | MediMush product | Eureka product |
|---|---|---|
| IL1α | 0.173 ± 0.033 | 0.003 |
| IL1β | 0.168 ± 0.053 | 0.016 |

The MediMush product was markedly immunostimulatory. The Eureka product showed some immunostimulation but was significantly weaker than the MediMush product. The MediMush product induced production of 58 times more IL1α and 20 times more IL1-β than Eureka.

Assay of Fractions

The filtrate was tested so that molecules greater than the filter cut off would not be present in the assay. The results are presented as absorbances and give only a relative immunostimulatory indication. No absolute value exists to calibrate such an assay.

TABLE 4

| Nominal Mwt | Filtrate MWt less than: | IL1α stimulation | IL1β stimulation |
|---|---|---|---|
| 1,000,000 | 3,000,000 | 0.082 | 0.073 |
| 300,000 | 900,000-1,800,000 | 0.086 | 0.040 |
| 100,000 | 300,000-900,000 | 0.07 | 0.071 |
| 50,000 | 150,000-300,000 | 0.086 | 0.066 |

All filtrate materials showed significant immunostimulation.

All filtrate materials showed significant immunostimulation.

Example 5

In order to compare two different production methods, the immune stimulating activity of the MediMush product prepared as described in example 1 was compared to the immune stimulating activity of a polysaccharide composition, which had not been subjected to size fractionation.

This product was prepared by cultivating Lentinus edodes in liquid culture as described in example 1. To the supernatant thus obtained around 2 volumes of absolute ethanol was added to precipitate the product. The precipitate was removed, washed with absolute ethanol and re-suspended in distilled water.

The immune stimulation assay was performed as described in example 4. The results using the MediMush product is given in table 5 and the results using the precipitated product are given in table 6.

TABLE 5

| Sample | MediMush product | Eureka product |
| --- | --- | --- |
| IL1a | 0.173 ± 0.033 | 0.003 |
| IL1b | 0.168 ± 0.053 | 0.016 |

TABLE 6

| Sample | Precipitated product | Eureka product |
| --- | --- | --- |
| IL1a | 0.166 | 0.023 |
| IL1b | 0.159 | 0.078 |

The assays were not performed in parallel and the numerical values obtained can therefore not be compared. However, since Eureka was used as a reference in both studies, the results may be compared as fold enhancement compared to Eureka. These values are given in table 7 below. As is apparent, both compositions were significantly more immune stimulating than Eureka. However, the MediMush product was more immune stimulating than the precipitated product.

TABLE 7

| Sample | MediMush:Eureka | Precipitated product:Eureka |
| --- | --- | --- |
| IL1a | 57.67 | 7.22 |
| IL1b | 19.69 | 2.04 |

Example 6

For a determination of immunostimulating characteristics, the following method may be used: 12 weeks old Sprague Dawley rats receives 1 mg of the composition according to the invention in 0.5 ml 0.09 saline (i.p.) 2 days before the immunisation. Control animals receives 1 mg casein. The animals are immunised with BSA (0.5 mg) in 0.25 "Freunds Complete Adjuvant" and blood samples are obtained after 11 days for measurement of the antibody response. The specific anti-BSA antibody concentration is determined against an absolute standard of antibody BSA by means of "sandwich" ELISA.

Example 7a

Protocol for Cultivation of Agaricus sp.

Cultivation Conditions:
Temperature: 25° C.±1° C.
pH: Medium pH
Water: Tap water
Medium: Glucose 30 g/l;
Mycological peptone 10 g/l;
Yeast extract 6 g/l
Malt extract 6 g/l Fermenter (3 Litres) Cultivation of Agaricus sp.

Place 1.7 litres of the medium in the fermenter and sterilise at 121° C. for 20 mins. Set the fermentation conditions: 25° C., 200-300 rpm and air at 0.2-0.5 wm. Inoculate the fermenter using 6-8 days old shake flask containing the fermentation medium or a similar medium that will promote good growth. Add a suitable antifoam agent when required (normally throughout the run). Harvests after 6-8 days Harvesting of Agaricus sp.

Biomass: Remove the biomass from the broth using a nylon cloth with pore size 45 as a filter medium. Wash the biomass thoroughly with water and dry in a microwave oven set at defrost until dry (normal sample size will require about 15 mins). Store in a desiccator until cool and weigh.

Fermentation liquor: The concentration of immunostimulating agent in the fermentation liquor is determined by ppt with abs ethanol. Sterile, distilled water is added if necessary to adjust the concentration to the desired level. The resulting liquid is autoclave and stored.

Medical grade: Pass the biomass-free fermentation liquor through a UF filter having a mwt cut-off such as for example 300 kD. When 70-80% of the liquid has been removed add water to the retentate to wash the solution. Repeat until the solution has lost much (most of) its colour and appears clean.

Example 7b

Agaricus blazei was cultivated as described in Example 7a, in liquid culture. After cultivation the biomass was separated from the rest of the fermentation broth by filtration. The supernatant was subjected to centrifugal filtration using filters with different mwt cut offs. The first product (denoted MediMush product II) was obtained by removing all components below 100 kD with the remaining liquid containing the product MediMush II. The second product (denoted MediMush product III) was obtained by removing all components from the supernatant having a mwt below 1 kD with the remaining liquid containing "Medimush product III".

Samples were hydrolysed to their constituent monosaccharides in 1N HCl at 100° C. The hydrolysates were analysed by HPLC using a Dionex MA-1 column with 600 mM NaOH as the mobile phase; detection was by pulsed amperometry.

The major monosaccharides of the MediMush products II and III were mannose and glucose and some galactose. Table B displays the relative monosaccharide content of the MediMush products II and III.

TABLE B

| SAMPLE | MANNOSE | GLUCOSE | GALACTOSE |
|---|---|---|---|
| MediMush II | 1 | 18 | 0 |
| MediMush III | 12 | 40 | 1 |

Example 8

*Ganoderma lucidum* was cultivated in a similar way as the *Agaricus* fungus as described in Example 7a, in liquid culture. After cultivation the biomass was separated from the rest of the fermentation broth by filtration. The supernatant was subjected to centrifugal filtration, as illustrated in Example 7a. The first product (denoted MediMush product IV) was obtained by removing all components below 100 kD with the remaining liquid containing the product MediMush IV. The second product (denoted MediMush product V) was obtained by removing all components from the supernatant having a mwt below 1 kD with the remaining liquid containing "Medimush product V".

Samples were hydrolysed to their constituent monosaccharides in 1N HCl at 100° C. The hydrolysates were analysed by HPLC using a Dionex MA-1 column with 600 mM NaOH as the mobile phase; detection was by pulsed amperometry.

The major monosaccharides of the MediMush products IV and V were mannose and glucose and some galactose. Table C displays the relative monosaccharide content of the MediMush products IV and V.

TABLE C

| SAMPLE | MANNOSE | GLUCOSE | GALACTOSE |
|---|---|---|---|
| MediMush IV | 1 | 1 | 0 |
| MediMush V | 3 | 5 | 1 |

Example 9

The Effect of Oral and Intraperitoneal Medimush Product Treatment on Proinflammatory Cytokine Production By Mouse Peritoneal Exudates Cells (PEC) and Splenocytes.

Materials and Methods:

Mice: Twenty-four, 5 week-old, male mice were used in these studies. They were purchased from the Division of Laboratory Animal Medicine, Louisiana State University. All studies were conducted in accordance with regulations as described in LSU IACUC protocol 04-120.

Medimush Product treatment Mice were divided into four groups. Group 1 received 2 mg/kg lentinian in 0.15 M NaCl, intraperitoneally (i.p.), group 2 received an equal volume of saline i.p., group 3 received 10 mg/kg Medimush Product in water by gastic gavage (oral) and group 4 received an equal volume of water orally. All mice received treatment once daily for 5 days. Twenty four hours after the last treatment the mice were bled and euthanized for cell isolation.

Isolation and stimulation of peritoneal exudates cells (PEC): PEC were collected by peritoneal lavage as previously described (1). Cells were concentrated to $1\times10^6$/mL in RPMI 1640 supplemented with 2 mM L-glutamine, 100 units/mL penicillin and 100 µg/mL streptomycin (medium) and distributed to 24 well tissue culture plates at 1 mL/well. Plates were centrifuged at 1200×g for 10 min and placed at 37° C., 5% $CO_2$ for 2 hours. Medium was discarded and the wells washed once with warm medium and replaced with 1.5 mL warm medium supplemented with 10% fetal bovine serum (Hyclone, Inc. Logan, Utah) (complete medium). Half the wells from each group were treated with *E. coli* lipopolysaccharide (LPS; Sigma Chemical Co., St. Louis, Mo.) at 10 ng/ml and the cells were placed at 37° C., 5% $CO_2$ for 12 or 24 hours. The phenotype of the cells was determined by flow cytometry using antibodies to CD3 and CD14 (eBioscience, San Diego, Calif.) labeled with phycoerythrin and anti-mouse IgG labeled with fluorescein (Jackson ImmunoResearch, Avondale, Pa.).

Isolation and stimulation of splenocytes: Spleens were harvested from each mouse. A portion was snap frozen for future mRNA analysis. The remaining spleens were pooled by group and crushed through a 70 µm nylon screen (Becton Dickenson Labware, Franklin Lakes, N.J.). Splenocytes were washed once and the pellet resuspended in buffered ammonium chloride for 5 min on ice. Cells were washed twice and resuspended at $4\times10^7$/mL in complete medium distributed to 24 well tissue culture plates at 1.5 mL/well. Representative wells were stimulated with *E. coli* LPS at 10 ng/ml or Concanavilin A (ConA; Sigma Chemical Co.) at 5 µg/mL and the cells were placed at 37° C., 5% $CO_2$ for 12 or 24 hours.

ELISA for cytokines. Cytokine ELISA for TNFα, IL-1β, IL-6 and IL-12 were conducted on serum and culture supernatants exactly as described by the manufacturer (eBioscience). Undiluted supernatants were tested in triplicate. Serum was diluted 1:10 for testing.

Results and Discussion

Medimush Product had no statistically significant effect on their growth as measured by weight gain (Table 1). However, i.p. Medimush Product had an effect on the number and phenotype of the cells isolated from the peritoneum lavage. Orally exposed mice and those that received saline i.p were relatively similar; however, there was a increase in the total number of cells isolated from the peritoneum of i.p. Medimush Product treated mice (data not shown). The increased number of cells was due mainly to an increase in neutrophils in the population (Table 2). The relative contribution to the observed results by the PMN compared to macrophage cannot be estimated at this time, but might effect the difference observed differences in the i.p. groups. In contrast, the number and phenotype of the oral groups were very similar and their comparisons should be statistically valid.

Intraperitoneal (i.p.) Medimush Product treatment caused a 4-fold increase in TNFα production at 12 hours by peritoneal exudate cells (PEC) (Table 3) and a 3-fold increase by splenocytes (Table 4) as well as increasing the amount of TNFα produced in response to LPS treatment in vitro by PEC (30% increase) and splenocytes (2-fold). Oral Medimush Product treatment had no significant effect on TNFα production by PEC or splenocytes. Interestingly, there was a significant decrease (20%) in TNFα production by PEC following in vitro LPS stimulation (Table 4). These results indicate that the effect on TNFα may be initiated at the local level and/or require direct exposure to Medimush Product.

Both oral and i.p. Medimush Product treatment significantly enhance IL-1β production by PEC (18-fold and 6-fold, respectively; Table 4). In addition, IL-1β in response to in vitro LPS was also increased more than 3-fold in ip treated mice Like TNF, IL-1β production by PEC from mice exposed to oral Medimush Product and stimulated in vitro LPS was decreased (2-fold).

Splenocytes from treated and untreated mice produce small amounts of IL-1β in the first 12 hours of culture. When mice were exposed to Medimush Product, either orally or i.p., splenocytes from the mice were stimulated to produce IL-1β by treatment with either LPS or ConA (a T cell mitogen).

In general, Medimush Product treatment had effects on IL-6 production by PEC, although this was only statistically significant in the non-LPS treated cells (Table 7). In contrast, IL-6 production was modestly elevated by unstimulated splenocytes but was modestly decreased by LPS or Con A stimulated splenocytes, both oral and i.p. exposure. IL-6 levels continued to rise over the next 12 hours of culture (Tables 9 and 10).

Interleukin 12 production at 12 hours was at the limit of detection of the assay except in ConA stimulated splenocyte cultures (Table 12). In the i.p. Medimush Product exposure, mice produce a significant amount of IL-12 in response to LPS.

Oral Medimush Product exposure generally decreased pro-inflammatory cytokine production by PEC and increased pro-inflammatory production by splenocytes suggesting the systemic response to Medimush Product (oral) may be different from the local responses measured in previous studies (nasal, i.p., i.v.).

Medimush Product administered i.p and orally could not be directly compared because the dosage of Medimush Product was not equivalent.

REFERENCE

1. Coligan, J E, Kruisbeek, A M, Margulies, D H, Shevach, E M, Strober, W (eds.). 1994. "in vitro assays for mouse lymphocytes" in Current Protocols in Immunology, John Wiley & Sons, Inc., Indianapolis, Ind., p 3.15.4

TABLE 1

The effect of Medimush Product treatment on weight gain.

| | Percent increase in weight | | |
|---|---|---|---|
| Route | control[a] | Medimush Product | p= |
| intraperitoneal | 10.5 ± 3.9 | 10.0 ± 1.1 | 0.8425 |
| oral | 11.3 ± 5.6 | 12.1 ± 4.0 | 0.3717 |

[a]0.15 M saline was used as a control for intraperitoneal injections and distilled water was used as a control for oral exposure.
** indicates that treatment is significantly different from the control.

TABLE 2

The phenotype of the cells placed in culture.

| | | Percent Lymphocytes | | | Monocytes/ |
|---|---|---|---|---|---|
| Route | in vitro Treatment | T cells[a] | B cells[b] | PMN[c] | Macrophages[d] |
| intraperitoneal | control[e] | 14 | 17 | 46 | 18 |
| intraperitoneal | Medimush Product | 4 | 3 | 84 | 6 |
| oral | control[e] | 14 | 16 | 48 | 15 |
| oral | Medimush Product | 20 | 25 | 37 | 18 |

[a]as determined by CD3 staining
[b]as determined by surface immunoglobulin staining
[c]based on flow cytometry side scatter
[d]based on bright staining with CD14
[e]0.15 M saline was used as a control for intraperitoneal injections and distilled water was used as a control for oral exposure.

TABLE 3

The effect of Medimush Product treatment on TNFα production by peritoneal exudate cells (PEC) following 12 hours of culture.

| | | TNFα production (pg/ml) by treatment[a] | | |
|---|---|---|---|---|
| Route | in vitro Treatment | control[b] | Medimush Product | p=[c] |
| intraperitoneal | none | 108 ± 4 | 428 ± 30** | 0.0036 |
| intraperitoneal | LPS | 407 ± 40 | 537 ± 50** | 0.0314 |
| oral | non | 320 ± 5 | 353 ± 20 | 0.1565 |
| oral | LPS | 469 ± 38 | 380 ± 23** | 0.0147 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 4

The effect of Medimush Product treatment on TNFα production by splenocytes following 12 hours of culture.

| | | TNFα production (pg/ml) by treatment[a] | | |
|---|---|---|---|---|
| Route | in vitro Treatment | control[b] | Medimush Product | p=[c] |
| intraperitoneal | none | 40 ± 9 | 119 ± 4** | 0.0084 |
| intraperitoneal | LPS | 174 ± 10 | 347 ± 8** | 0.0006 |
| intraperitoneal | Con A | 296 ± 10 | 390 ± 10** | 0.0191 |
| oral | none | 34 ± 6 | 35 ± 0 | 0.7734 |
| oral | LPS | 114 ± 4 | 160 ± 5** | 0.0026 |
| oral | ConA | 349 ± 15 | 351 ± 6 | 0.7337 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 5

The effect of Medimush Product treatment on IL-1β production by peritoneal exudate cells (PEC) following 12 hours of culture.

| | | IL-1β production (pg/ml) by treatment[a] | | |
|---|---|---|---|---|
| Route | in vitro Treatment | control[b] | Medimush Product | p=[c] |
| intraperitoneal | none | 25 ± 8 | 146 ± 7** | 0.0006 |
| intraperitoneal | LPS | 225 ± 16 | 751 ± 152** | 0.0323 |
| oral | none | 5 ± 2 | 93 ± 7** | 0.0015 |
| oral | LPS | 487 ± 15 | 227 ± 1.1** | 0.0017 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 6

The effect of Medimush Product treatment on IL-1β production by splenocytes following 12 hours of culture.

| | | IL-1β production (pg/ml) by treatment[a] | | |
|---|---|---|---|---|
| Route | in vitro Treatment | control[b] | Medimush Product | p=[c] |
| intraperitoneal | none | 1 ± 1 | 5 ± 1** | 0.0084 |
| intraperitoneal | LPS | 2 ± 0 | 49 ± 9** | 0.0015 |

TABLE 6-continued

The effect of Medimush Product treatment on IL-1β production by splenocytes following 12 hours of culture.

| | | IL-1β production (pg/ml) by treatment[a] | | |
|---|---|---|---|---|
| Route | Treatment | control[b] | Medimush Product | p=[c] |
| intraperitoneal | Con A | 4 ± 2 | 13 ± 3 | 0.0717 |
| oral | none | 3 ± 1 | 3 ± 0 | 0.7811 |
| oral | LPS | 3 ± 0 | 11 ± 1** | 0.0213 |
| oral | ConA | 3 ± 1 | 11 ± 2 | 0.0969 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 7

The effect of Medimush Product treatment on IL-6 production by peritoneal exudate cells (PEC) following 12 hours of culture.

| | | IL-6 production (pg/ml) by treatment[a] | | |
|---|---|---|---|---|
| Route | Treatment | control[b] | Medimush Product | p=[c] |
| intraperitoneal | none | 567 ± 25 | 320 ± 33** | 0.0194 |
| intraperitoneal | LPS | 265 ± 15 | 286 ± 54 | 0.5657 |
| oral | non | 288 ± 30 | 247 ± 30** | 0.0027 |
| oral | LPS | 258 ± 31 | 209 ± 17 | 0.8763 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 8

The effect of Medimush Product treatment on IL-6 production by splenocytes following 12 hours of culture.

| | | IL-6 production (pg/ml) by treatment[a] | | |
|---|---|---|---|---|
| Route | Treatment | control[b] | Medimush Product | p=[c] |
| intraperitoneal | none | 132 ± 2 | 344 ± 30** | 0.0098 |
| intraperitoneal | LPS | 299 ± 10 | 367 ± 31 | 0.0853 |
| intraperitoneal | Con A | 393 ± 19 | 233 ± 24** | 0.0029 |
| oral | none | 114 ± 2 | 199 ± 7** | 0.0014 |
| oral | LPS | 367 ± 31 | 329 ± 11** | 0.0124 |
| oral | ConA | 233 ± 24 | 248 ± 25** | 0.0284 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 9

The effect of Medimush Product treatment on IL-6 production by peritoneal exudate cells (PEC) following 12 hours of culture.

| | | IL-6 production (pg/ml) by treatment[a] | | |
|---|---|---|---|---|
| Route | Treatment | control[b] | Medimush Product | p=[c] |
| intraperitoneal | none | 101 ± 2 | 272 ± 5** | 0.0009 |
| intraperitoneal | LPS | 624 ± 15 | 932 ± 17 | 0.0011 |
| oral | none | 764 ± 10 | 852 ± 43 | 0.0833 |
| oral | LPS | 835 ± 29 | 760 ± 77 | 0..3680 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 10

The effect of Medimush Product treatment on IL-6 production by splenocytes following 12 hours of culture.

| | | IL-6 production (pg/ml) by treatment[a] | | |
|---|---|---|---|---|
| Route | Treatment | control[b] | Medimush Product | p=[c] |
| intraperitoneal | none | 105 ± 6 | 638 ± 18** | 0.0004 |
| intraperitoneal | LPS | 218 ± 16 | 524 ± 33** | 0.0042 |
| intraperitoneal | Con A | 567 ± 7 | 835 ± 39** | 0.0029 |
| oral | none | 117 ± 5 | 190 ± 3** | 0.0007 |
| oral | LPS | 174 ± 5 | 266 ± 3** | 0.0065 |
| oral | ConA | 326 ± 6 | 510 ± 11** | 0.0039 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 9

The effect of Medimush Product treatment on IL-12 production by peritoneal exudate cells (PEC) following 12 hours of culture.

| | | IL-12 production (pg/ml) by treatment[a] | | |
|---|---|---|---|---|
| Route | Treatment | control[b] | Medimush Product | p=[c] |
| intraperitoneal | none | 3 ± 1 | 6 ± 1 | 0.0509 |
| intraperitoneal | LPS | 2 ± 2 | 14 ± 7 | 0.0734 |
| oral | non | 6 ± 3 | 3 ± 2** | 0.02512 |
| oral | LPS | 1 ± 1 | 2 ± 2 | 0.5627 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
**statistically significant at p < 0.005

TABLE 10

The effect of Medimush Product treatment on IL-12 production by splenocytes following 12 hours of culture.

| | | IL-12 production (pg/ml) by treatment[a] | | |
|---|---|---|---|---|
| Route | Treatment | control[b] | Medimush Product | p=[c] |
| intraperitoneal | none | 1 ± 1 | 11 ± 5 | 0.1017 |
| intraperitoneal | LPS | 13 ± 9 | 2 ± 1 | 0.2611 |
| intraperitoneal | Con A | 96 ± 11 | 86 ± 8 | 0.4155 |
| oral | none | 2 ± 2 | 0 ± 0 | 0.3855 |

TABLE 10-continued

The effect of Medimush Product treatment on IL-12 production by splenocytes following 12 hours of culture.

| | | IL-12 production (pg/ml) by treatment[a] | | |
|---|---|---|---|---|
| Route | in vitro Treatment | control[b] | Medimush Product | p=[c] |
| oral | LPS | 4 ± 4 | 1 ± 1 | 0.4405 |
| oral | ConA | 71 ± 11 | 80 ± 7 | 0.2293 |

[a]Limit of detection 8 pg/ml
[b]0.15 M saline was used as a control for intraperitoneal injections and distilled water was used as a control for oral exposure.
[c]paired t test using StatXact v 6.0, Cytel Sudio, 2004
** statistically significant at p < 0.005

Example of Functional Food Products

The invention will now be further illustrated by the description of suitable embodiments of the preferred functional food products for use in the invention. It is believed to be well within the ability of the skilled person to use the teaching provided therewith to prepare other products of the invention.

Example 10

Bar 75 g of dark chocolate are melted at 70 degrees C. and subsequently mixed with 600 mg of Medimush product. The mixture is poured into a bar shaped mold and cooled overnight.

Example 11

Milkshake 100 ml of vanilla flavored ice-cream are mixed with 100 ml of cooled milk, 10 ml of strawberry syrup and 1 ml extracellular liquid from mushroom cultivation. The mixture is fed through a blender and immediately served.

Example 12

Nougat Bar
Ingredient weight (g)
Water 70
Hyfoama (emulsifier) 3.5
Gelatin 2.0
Sugar 515
Glucose syrup 60DE 250
Glucose syrup 35DE 250
Skimmed milk powder 115
Fat 50
1 g extracellular liquid from mushroom cultivation Method of preparation: dissolve hyfoama and gelatin in water add 150 g of sugar and beat to foam, heat remaining sugar to 130 degrees C. and add slowly to foam. Add fat, glucose syrup, milkpowder and 1 g extracellular liquid from mushroom cultivation. Allow to cool and divide in bars of 50 g.

Example 13

Fruit Drink

11 Ingredients 200 g fruit juice concentrate (banana, pine apple, orange, grape, apricot, lemon, passion fruit, guava, mango) 5 g fructose 1 g insulin 10 g, 0.1 g Medimush product IV, 0.9 g plant sterol fatty acid ester (=0.54 g sterol equivalents) 5 g lecithin, 1.5 g calcium lactate 775 g water

The invention claimed is:

1. An isolated, aqueous liquid immune stimulating composition comprising a mixture of polysaccharides comprising the monosaccharide units galactose, mannose and glucose,
    wherein: the majority of the polysaccharides of the composition have a molecular weight of at least 1,000 Da wherein a first part of said polysaccharides have a molecular weight of less than 1,000,000 Da, wherein a second part of said polysaccharides have a molecular weight of at least 1,000,000 Da, wherein said mixture of polysaccharides comprises the monosaccharides galactose, mannose and glucose in the ratio 1:0.033 to 500:1 to 50, and wherein the composition is produced by a method comprising the steps of;
    a) cultivating a fungus of the genus Lentinus in a liquid growth medium under appropriate conditions to provide a suitable chemical and physical environment supporting the growth of a fungus of the genus Lentinus in the liquid growth medium,
    b) isolating the composition from said liquid growth medium by one or more size fractionation steps, and
    c) retaining said composition for further use.

2. The composition according to claim 1, wherein the one or more size fractionation steps comprise a method involving ultracentrifugation, ultrafiltration, microfiltration or gel filtration.

3. The composition according to claim 1, wherein the fungus of the genus Lentinus is Lentinus edodes.

4. The composition according to claim 1, wherein the majority of the polysaccharides of the composition have a molecular weight of at least 50,000 Da.

5. The composition according to claim 1, wherein the majority of the polysaccharides of the composition have a molecular weight of at least 100,000 Da.

6. A method of producing a composition according to claim 1, said method comprising the steps of
    a) cultivating a fungus of the genus Lentinus in a liquid growth medium under appropriate conditions to provide a suitable chemical and physical environment supporting the growth of a fungus of the genus Lentinus in a liquid growth medium, and
    b) isolating the composition from said liquid growth medium by one or more size fractionation steps and retaining said composition for further use.

7. The method according to claim 6, wherein said separation is achieved by a method step comprising ultracentrifugation, ultrafiltration, microfiltration or gel filtration.

8. A pharmaceutical composition comprising the composition according to claim 1 and a pharmaceutically acceptable carrier.

9. A method of treatment of an individual
    i) diagnosed with an immune compromised condition; and/or
    ii) at risk of contracting an immune compromised condition; and/or
    iii) recovering from surgery or illness and at risk of contracting an immune compromised condition; and/or
    iv) diagnosed with or at risk of contracting acquired immunodeficiency syndrome,
    said method comprising the steps of administering to said individual the composition according to claim 1 in an amount effective in treating said immune compromised condition or said syndrome or effective in boosting the immune system of said individual.

10. A kit comprising the composition according to claim 1 and a dosage regime instruction with guidelines for dose and time administration.

* * * * *